(12) United States Patent
Baba et al.

(10) Patent No.: US 11,124,757 B2
(45) Date of Patent: *Sep. 21, 2021

(54) MICROORGANISM CULTURE SHEET AND MANUFACTURING METHOD THEREFOR

(75) Inventors: Takuma Baba, Tokyo (JP); Mai Kinoshita, Tokyo (JP); Rui Saito, Tokyo (JP); Tetsuji Ueki, Tokyo (JP)

(73) Assignee: KIKKOMAN CORPORATION, Noda (JP)

( * ) Notice: Subject to any disclaimer, the term of this patent is extended or adjusted under 35 U.S.C. 154(b) by 472 days.

This patent is subject to a terminal disclaimer.

(21) Appl. No.: 13/383,669

(22) PCT Filed: Jul. 14, 2010

(86) PCT No.: PCT/JP2010/061897
§ 371 (c)(1),
(2), (4) Date: Jan. 12, 2012

(87) PCT Pub. No.: WO2011/007802
PCT Pub. Date: Jan. 20, 2011

(65) Prior Publication Data
US 2012/0107913 A1 May 3, 2012

(30) Foreign Application Priority Data

Jul. 14, 2009 (JP) .............................. JP2009-165431
Jul. 14, 2009 (JP) .............................. JP2009-165432

(51) Int. Cl.
*C12M 1/22* (2006.01)
*C12N 1/00* (2006.01)
(Continued)

(52) U.S. Cl.
CPC .............. *C12N 1/00* (2013.01); *C12M 23/10* (2013.01); *C12M 23/38* (2013.01); *C12M 25/14* (2013.01); *G01N 21/78* (2013.01)

(58) Field of Classification Search
CPC .... C12N 2535/10; C12N 5/0068; C12N 1/20; C12N 5/0018; C12M 23/10; C12M 25/14;
(Continued)

(56) References Cited

U.S. PATENT DOCUMENTS 3,827,942 A * 8/1974 Janik ........................ C12N 1/00
435/253.6
4,945,061 A * 7/1990 Iskander ................ C12M 23/10
435/305.1
(Continued)

FOREIGN PATENT DOCUMENTS

EP 1179586 A1 2/2002
EP 1743975 * 1/2007
(Continued)

OTHER PUBLICATIONS http://www.dictionary.com/browse/fixed, accessed Mar. 22, 2016.*
(Continued)

*Primary Examiner* — Erin M. Bowers
(74) *Attorney, Agent, or Firm* — Locke Lord LLP

(57) ABSTRACT

A microorganism culture sheet is provided which can limit the use of a costly cultivation material to a necessary portion, which has simple production at the time of manufacture, and can be simply and stably used by a user. The microorganism culture sheet of the present invention is a microorganism culture sheet comprising a base sheet, a culture layer formed on top of the base sheet, and a cover sheet that covers the culture layer, and the culture layer is pattern-formed with an application liquid comprising a polyvinylpyrrolidone and at least on selected from the group consisting of a gelling agent, a nutrient component, a color indicator, a selective agent and a substrate.

19 Claims, 15 Drawing Sheets

(51) Int. Cl.
*C12M 1/12* (2006.01)
*C12M 1/00* (2006.01)
*G01N 21/78* (2006.01)

(58) Field of Classification Search
CPC ...... C12M 23/04; C12M 25/02; C12M 23/38; C12M 23/12; C12M 23/22; C12M 29/04; C12M 33/04; C12M 41/03; C12Q 1/04; C12Q 1/24; C12Q 1/045; C12R 1/01
See application file for complete search history.

(56) References Cited

U.S. PATENT DOCUMENTS

| | | | |
|---|---|---|---|
| 5,622,761 A * | 4/1997 | Cole | C09J 7/38 428/41.9 |
| 5,856,176 A * | 1/1999 | Mathus | C12M 23/10 220/755 |
| 2010/0159597 A1 | 6/2010 | Kuroda et al. | |

FOREIGN PATENT DOCUMENTS

| | | | |
|---|---|---|---|
| JP | 02-49705 B2 | | 10/1990 |
| JP | 08-280377 A | | 10/1996 |
| JP | H08-280377 | * | 10/1996 |
| JP | H09-19282 A | | 1/1997 |
| JP | 09-075063 A | | 3/1997 |
| JP | 09-206062 A | | 8/1997 |
| JP | 09-206202 | * | 8/1997 |
| JP | 2004-515236 A | | 5/2004 |
| JP | 2008-193919 | * | 8/2008 |
| JP | 2008-193919 A | | 8/2008 |
| JP | 2009-153501 A | | 7/2009 |
| WO | WO-1982/02563 A1 | | 8/1982 |
| WO | WO-2001/38559 A2 | | 5/2001 |
| WO | WO-2001/44437 A1 | | 6/2001 |
| WO | WO-2008/153063 A1 | | 12/2008 |

OTHER PUBLICATIONS

Steane, http://web.archive.org/web/20060424082858/http://www.biotopics.co.uk/microbes/tech.html, archived Apr. 24, 2006, accessed Dec. 5, 2016.*

Wikipedia, https://en.wikipedia.org/wiki/Petri_dish, archived Dec. 17, 2008, accessed Jun. 19, 2019.*

International Search Report issued in PCT/JP2010/061897 dated Sep. 14, 2010.

Extended European Search Report issued in corresponding European Patent Application No. 10799860.1, dated Mar. 12, 2014.

Office Action dated Feb. 9, 2018, issued to EP Patent Application No. 10799860.1.

* cited by examiner

FIG. 1
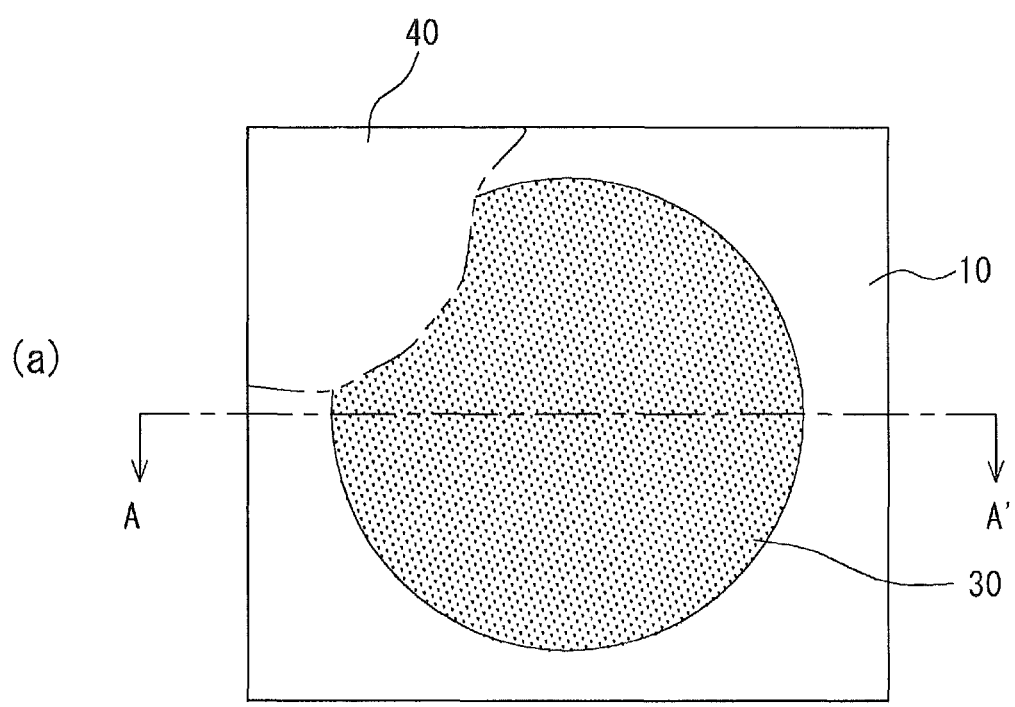
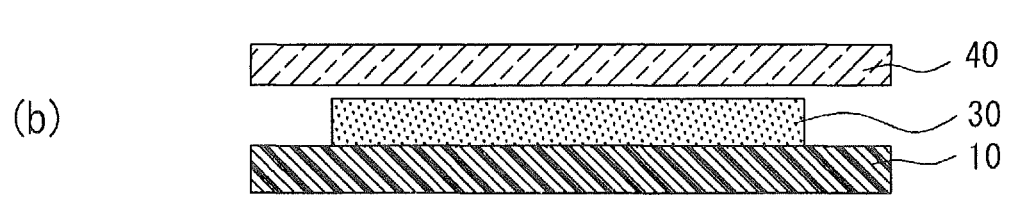

FIG. 2
(a)
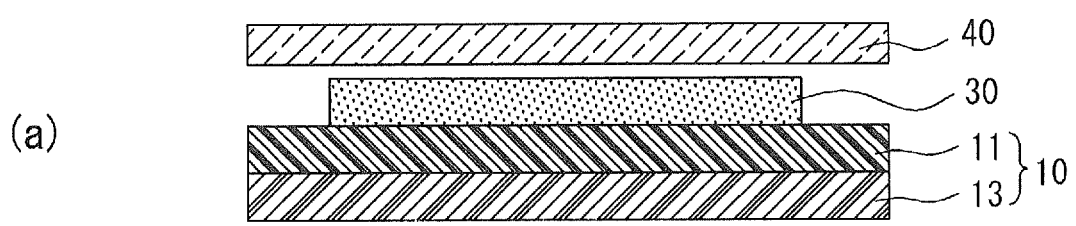
(b)
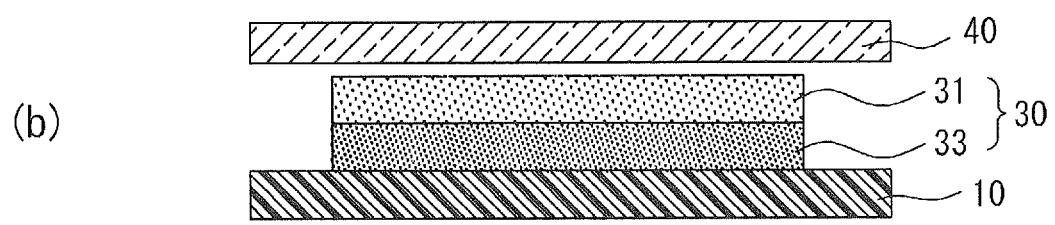

FIG. 9
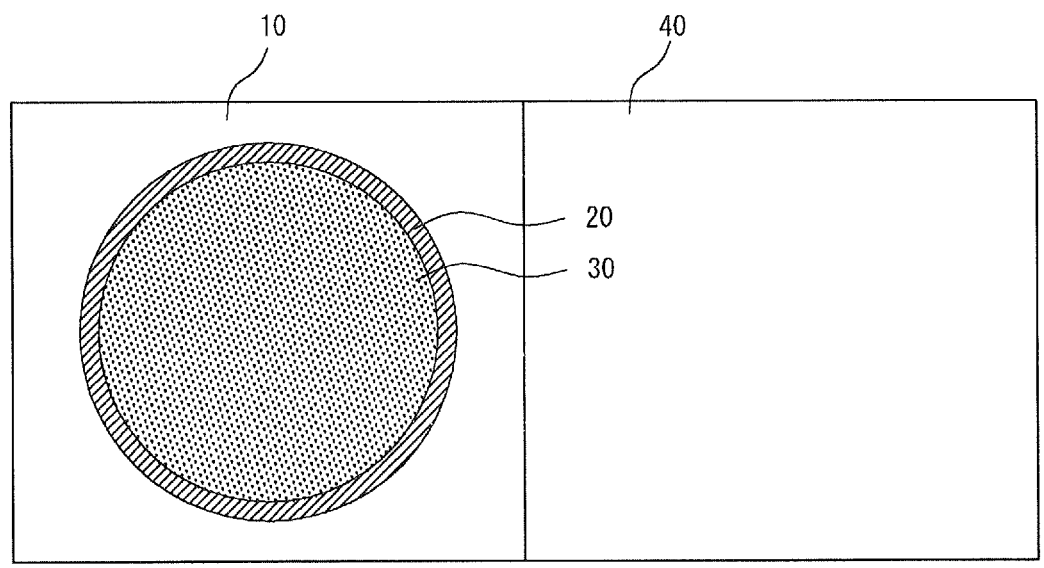
(a)
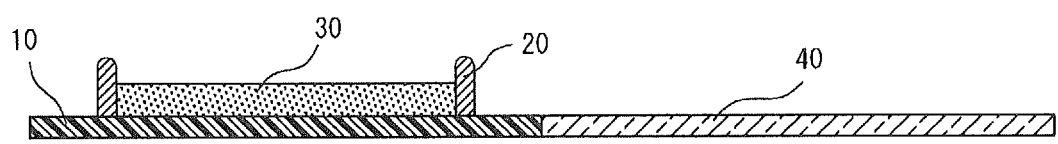
(b)
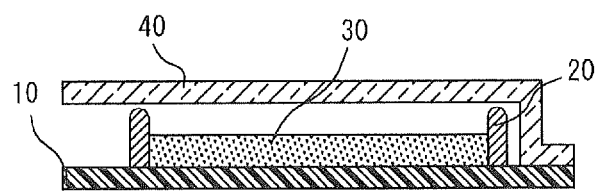
(c)

MICROORGANISM CULTURE SHEET AND MANUFACTURING METHOD THEREFOR

CROSS REFERENCE TO RELATED APPLICATIONS

This application is a 371 US National Phase Application of PCT/JP2010/061897, filed Jul. 14, 2010, which claims priority to Japanese Patent Application No. JP 2009-165431, filed Jul. 14, 2009, and Japanese Patent Application No. JP 2009-165432, filed Jul. 14, 2009, the disclosures of each of which are expressly incorporated herein by reference in their entireties.

TECHNICAL FIELD

The present invention relates to a microorganism culture sheet which can be used for cell count testing and the like, and more specifically, relates to a microorganism culture sheet which, because the culture layer is pattern-formed on a predetermined area of the base sheet, has little waste of the culture materials, and further, has a simple operation.

BACKGROUND ART

As a method for confirming the presence of microorganisms, or as a method for measuring the microorganisms, there is the petri plate method. In the petri plate method, an agar medium formed on a dish which has been sterilized in advance is used, thus for high pressure steam sterilization of the agar medium, an autoclave or a laboratory for carrying out aseptic microorganism testing is required, and further, the operations of the microorganism testing of the preparation of the liquid sample from a sampling of the microorganisms, the dispensing and mixing with the culture medium, the cultivation and the counting and the like, require skill, thus, microorganism culture sheets which provide a dry medium making it possible to easily carry out microorganism testing without requiring a high degree off skill have been developed.

For example, Patent Publication 1 discloses a sheet-shaped culturing device provided with an adhesive layer to which a cold-water-soluble powder comprising a gelling agent or nutrients is uniformly adhered by an adhesive, on a waterproof substrate. This sheet-shaped culturing device was made in consideration of the problems that, according to a device of the prior art where a filter paper impregnated with a gelling agent and nutrients for growing microorganisms is adhered to a film by means of an adhesive layer, because the filter paper is not transparent, the counting of bacterial colonies is difficult, and further, it is difficult to isolate the individual colonies; and solves the problem of a device where a filter paper is interposed by a method of directly fixing the gelling agent and nutrient components via an adhesive. Moreover, Patent Publication 1 also discloses that when using the above sheet-shaped culturing device, the test liquid is spread so as to be confined to a specific region by temporarily placing a template such as a weighted circular ring on the cover sheet.

Patent Document 2 discloses a sheet-shaped culturing device consisting of a substrate, a pedestal comprising a non-absorbent culture surface formed on the top face of the substrate, and a cover sheet, where a culture medium is deposited on the culture surface and/or the cover sheet bottom surface. This sheet-shaped culturing device was made in consideration of the problem that, according to the method of the prior art where a cold-water-soluble powder is adhered to the substrate via an adhesive, it is not possible to maintain suitable concentrations of the constituent components of the culture medium such as the gelling agent, nutrient, inhibitor, indicator and the like because an agglomerate of irregular shape and dimension is formed. According to the sheet-shaped culturing device disclosed in Patent Document 2, the user, without requiring any special equipment or operations, can spread an aqueous sample that is uniformly shaped and sized. Further, in the Examples of Patent Document 2, a sheet-shaped culturing device is manufactured by the following method. First, after coating an application liquid which is a bouillon solution comprising a gum on the upper face of a pedestal base portion, the water was evaporated at 100° C. Next, a heat sensitive adhesive, polystyrene foam and a polyacrylate PSA were laminated onto the other face of the pedestal base portion, and the obtained laminate was die-cut with a diameter of 5.1 cm. After adhering this die-cut laminate onto the base face so that the PSA side was down, a cover sheet was adhered to the edges of the base material to produce the sheet-shaped culturing device.

Patent Document 3 discloses a microorganism culture device wherein a circular porous matrix layer and a water soluble polymer compound layer are laminated on a square adhesive sheet, and on this, a square transparent film is further disposed. In this microorganism culture device, by adding the liquid sample onto the porous matrix layer, the liquid sample is retained in the porous matrix layer. Then, the water content of the retained liquid sample dissolves the water soluble polymer compound layer adhered to the porous matrix layer, and a water soluble polymer compound solution is generated, to form an environment where microorganisms can grow due to the polymer compound solution and the growth nutrient components. Further, in this microorganism culture device, the microorganisms do not penetrate into the interior of the water soluble polymer composition layer because the dissolved water soluble polymer compound layer is a high viscosity solution, thus in the process of integrating the dissolved water soluble polymer compound layer and the porous matrix layer, the microorganisms are pushed to the surface of the porous matrix layer. Therefore, the colonies are formed at the surface or near the surface of the porous matrix layer. In this microorganism culture device, the above mentioned porous matrix layer is adhered to the adhesive sheet so as to be on top, and further, by covering with the transparent film so as to contact the above porous matrix layer, use as a sheet-form microorganism culture device with low weight and bulk, and further with easy handling becomes possible. Further, as the above mentioned water soluble polymer, a polyvinyl alcohol having a saponification degree of 75 to 95%, and a molecular weight of 25000 to 250000 is disclosed.

Patent Document 4 discloses a microorganism culturing sheet wherein a culture layer is formed by applying a culture mixture and a water absorbent resin on the entire surface of a waterproof base sheet, and an outer frame layer is formed of a hydrophobic ink for regulating the spread of the inoculated test liquid on the culture layer. Further, in the Examples of Patent Document 4, using a transparent biaxially oriented polyester film with a thickness of 100 μm as a base sheet, a culture layer forming coating slip wherein a nutrient component and a triphenyl tetrazolium chloride are combined in a toluene solution of a polyethylene oxide, is coated onto the base sheet by a comma coater so that when dry, the coated amount is 30 g/m², and on the formed culture layer, a doughnut shaped pattern having an outer diameter of 70 mm and an inner diameter of 50 mm, which forms an outer frame layer, is formed by screen printing of hydrophobic ink.

Patent Document 1: Japanese Examined Patent Application, Publication No. H2-49705

Patent Document 2: Japanese Unexamined Patent Application (Translation of PCT Application), Publication No. 2004-515236

Patent Document 3: International Publication No. WO01/044437

Patent Document 4: Japanese Unexamined Patent Application, Publication No. H8-280377

DISCLOSURE OF THE INVENTION

Problems to be Solved by the Invention

Because the culture material for microorganisms is costly, it is preferable to reduce the amount used. However, in Patent Document 4, the culture layer is laminated over the entire area of the base material film, and because the culture layer is also formed outside of the portions necessary for cultivation of the microorganisms, a waste of the costly material arises. Further, in Patent Document 2 and Patent Document 3, after coating the application liquid on the entire surface of the film, one portion thereof is die-cut, and what is adhered to the base material becomes the culture layer, thus waste of the material also arises.

Further, for a microorganism culture sheet, it is preferred that the processes when manufacturing be simple. In this point, in the culturing device disclosed in Patent Document 1 above, the culture layer is formed by uniformly adhering to the substrate, with an adhesive, a cold-water-soluble powder which is a gelling agent and a nutrient component; this can be said to be a simple method, but in this method the microorganisms can easily come into contact with the adhesive component. Therefore, it is possible for the adhesive component to exert an effect on the growth of the microorganisms, thus this cannot be said to be preferable. In contrast, in the sheet-shaped culturing device disclosed in Patent Document 2, the culture layer is formed by coating a bouillon solution comprising a guar bean gum as a gelling agent on top of the pedestal base comprising a polyester film or the like, without using an adhesive. However, in the sheet-shaped culturing device disclosed in Patent Document 2, as mentioned above, after coating the application liquid on the entire surface of the film, the die-cutting step is carried out, and the obtained die-cut product is adhered to the base material by an adhesive to form the culture layer, thus the manufacturing process is complex. In the microorganism culture device disclosed in Patent Document 3, the same procedure is carried out as in the sheet-shaped culturing device disclosed in Patent Document 2, thus the manufacturing process is also complex.

In the sheet-shaped culturing device disclosed in Patent Document 2, the culture medium solution includes water, thus it is necessary to carry out heat drying under high temperature conditions, thus there is the concern that the nutrient component, the gelling agent, the color indicator, the substrate and the base material may be decomposed by the heating. Therefore, the usable nutrient component, gelling agent, color indicator, substrate and base material are limited. This is the same for the microorganism culture device disclosed in Patent Document 3 which uses a polyvinyl alcohol aqueous solution. The microorganism culturing sheet disclosed in Patent Document 4 uses a toluene solution of polyethylene oxide as a culturing medium mixture, however, toluene is an organic solvent which also has a high boiling point exceeding 100° C., thus the materials which can be used are also limited.

Furthermore, the inoculation operation of the test liquid is preferably simple so that it can be carried out expeditiously. However, in the culturing device disclosed in Patent Document 1, in order to control the spreading of the test liquid, it is necessary to limit the test liquid to a specified area by temporarily applying a template such as a weighted circular ring onto the cover sheet, and this cannot be said to be a simple operation. Further, in the microorganism culture device disclosed in Patent Document 3, in order to suppress the spread of the test liquid, the culture layer is constituted of a porous matrix. Therefore, the water absorption time of the test liquid becomes long, and a loss arises in the user's operation time. Further, in the microorganism culture device disclosed in Patent Document 3, in order to prevent drying during cultivation, after the test liquid inoculation the culture layer is covered with the cover sheet, but because the above mentioned culture layer absorbs water and its volume increases, if the adhesive sheet and cover sheet are not adhered with care, a gap which may becomes a cause of drying during cultivation may arise. Further, if the culture layer after water absorption is pressed, the test liquid may seep out of the porous matrix, thus the user must carry out this operation carefully. Concerning this point, a loss during operation may easily arise.

In the microorganism culturing sheet disclosed in Patent Document 4, an outer frame layer is provided of a hydrophobic ink for regulating the spread of the inoculated test liquid. This outer frame layer is formed on top of the culture layer, thus the lower portion of the outer frame layer can become hydrated by dripping of the test liquid, and the outer frame layer may collapse, or the test liquid may seep to the lower portion and the outer boundary of the outer frame layer, and stable use is difficult.

Further, in microorganism testing, it is necessary to carry out an accurate count of the colonies. However, in Patent Document 1 and Patent Document 2, the culture layer is formed not only on the upper face of the paper base material, but also on the cover sheet, thus sufficient visibility may not be obtained. Further, in the microorganism culture device disclosed in Patent Document 3, because the culture layer is constituted of the porous matrix, the bacteria are entrapped in the matrix. Therefore, when the multiplication of the bacteria proceeds, it may be difficult to view the generated colonies, in particular, when the bacteria are close and multiply, it may be difficult to count the colonies.

The present invention was made in consideration of the above mentioned problems, and has the objective of providing a microorganism culture sheet which can limit the use of the costly culture material to the required portion, has a simple manufacturing process, and which a user can simply and stably use.

Means for Solving the Problems

The present invention, as a result of considering in detail a microorganism culture sheet, was completed and made by the findings that (1) the usage of the costly cultivation material can be reduced by pattern-forming by printing or applying the culture layer onto a base sheet; (2) a culture layer of a predetermined shape can be inexpensively and simply formed by pattern-forming, by using as the application liquid a polyvinylpyrrolidone solution comprising at least one selected from the group consisting of a gelling agent, a nutrient component, a color indicator, a selective agent, and a substrate; (3) deterioration of the combined components which may arise during solvent removal can be prevented by using an alcohol solution as the solvent used for the application liquid; and (4) the test liquid spreads to a regulated area merely by covering, without waiting for the water absorption of the test liquid and without using a ring-shaped template, by pattern-forming the culture layer, moreover, leaking of the test liquid can be prevented by further forming a frame layer.

Namely, the present invention provides a microorganism culture sheet having a base sheet, a culture layer formed on top of the base sheet, and a cover sheet that covers the culture layer, wherein the culture layer is pattern-formed of an application liquid comprising a polyvinylpyrrolidone, at least one selected from the group consisting of a gelling agent, a nutrient component, a color indicator, a selective agent, and a substrate.

Further, the present invention provides a method of manufacturing a microorganism culture sheet having a base sheet, a culture layer formed on top of the base sheet, and a cover sheet that covers the culture layer, comprising a culture layer forming step wherein an application liquid comprising at least one selected from the group consisting of a gelling agent, a nutrient component, a color indicator, a selective agent and a substrate, in an alcohol solution of a polyvinylpyrrolidone, is pattern-formed on top of the base sheet, and then the alcohol included in the application liquid is removed to form the culture layer.

The present invention also provides a method of manufacturing a microorganism culture sheet having a base sheet, a culture layer formed on top of the base sheet, and a cover sheet that covers the culture layer, wherein a frame layer consisting of a hydrophobic resin of a convex form is formed in advance at the base sheet so as to surround the outer boundary of the culture layer when the culture layer is formed, and after pattern-forming an application liquid comprising at least one selected from the group consisting of a gelling agent, a nutrient component, a color indicator, a selective agent, and a substrate, in an alcohol solution of a polyvinylpyrrolidone, the culture layer is formed by removing the alcohol included in the application liquid.

Effects of the Invention

According to the microorganism culture sheet of the present invention, the culture layer is pattern-formed on the base sheet, thus it becomes possible to limit the use of the culture material for the microorganisms to only the necessary portions, and the used amount of the costly material can be reduced. Further, according to the microorganism culture sheet of the present invention, the polyvinylpyrrolidone is an essential component of the application liquid, thus it is possible to inexpensively and simply pattern-form a culture layer of a predetermined shape. Furthermore, in the microorganism culture sheet of the present invention, the culture layer is pattern-formed, thus after instilling the test liquid, by quickly covering with the cover sheet, the test liquid naturally spreads over a predetermined area and the operability is excellent.

According to the first method of producing the microorganism culture sheet of the present invention, the culture layer is pattern-formed on top of the base sheet, thus it is possible to avoid waste of the costly material. Further, the pattern-forming is an inexpensive method such as printing or applying, thus it is possible to reduce the manufacturing costs. Furthermore, according to the first method of manufacturing the microorganism culture sheet of the present invention, when pattern-forming with the application liquid, an alcohol is used as the solvent, thus removal of the solvent is easy, and further, the solvent's boiling point is low, thus it is possible to effectively avoid the thermal decomposition of the combined components.

In the second method of manufacturing the microorganism culture sheet of the present invention, a frame layer consisting of a hydrophobic resin of a convex form is formed in advance at the base sheet so as to surround the outer boundary of the culture layer when the culture layer is formed, thus even when the test liquid is inoculated, the frame layer remains stable without collapsing, and has excellent working operability and stability. Further, according to the second method of producing the microorganism culture sheet of the present invention, the frame layer surrounding the outer boundary of the culture layer is formed on top of the base sheet, thus leaking of the test liquid can be more securely prevented, and the operational efficiency when inoculating can be improved.

BRIEF DESCRIPTION OF THE DRAWINGS

FIG. 1 is a drawing where 1(*a*) is a top view and 1(*b*) is a cross sectional view, showing one example of the microorganism culture sheet according to the present invention, showing a state where a circular culture layer is formed approximately in the center of the base sheet.

FIG. 2 is a cross sectional view showing one example of the microorganism culture sheet according to the present invention; 2(*a*) is a drawing showing a state where the base sheet has a multilayer structure; and 2(*b*) is a drawing showing a state where the culture layer has a multilayer structure.

FIG. 9 is a drawing showing one example of the microorganism culture sheet according to the present invention where 9(a) is a developed view and 9(b) is a cross sectional view, showing a state where the culture layer, surrounded by the frame layer at its outer boundary, is formed on top of the base sheet which is continuously provided with the cover sheet, and 9(c) is a cross sectional view showing a state where the cover sheet is folded so as to cover the culture layer.

Figure 3:
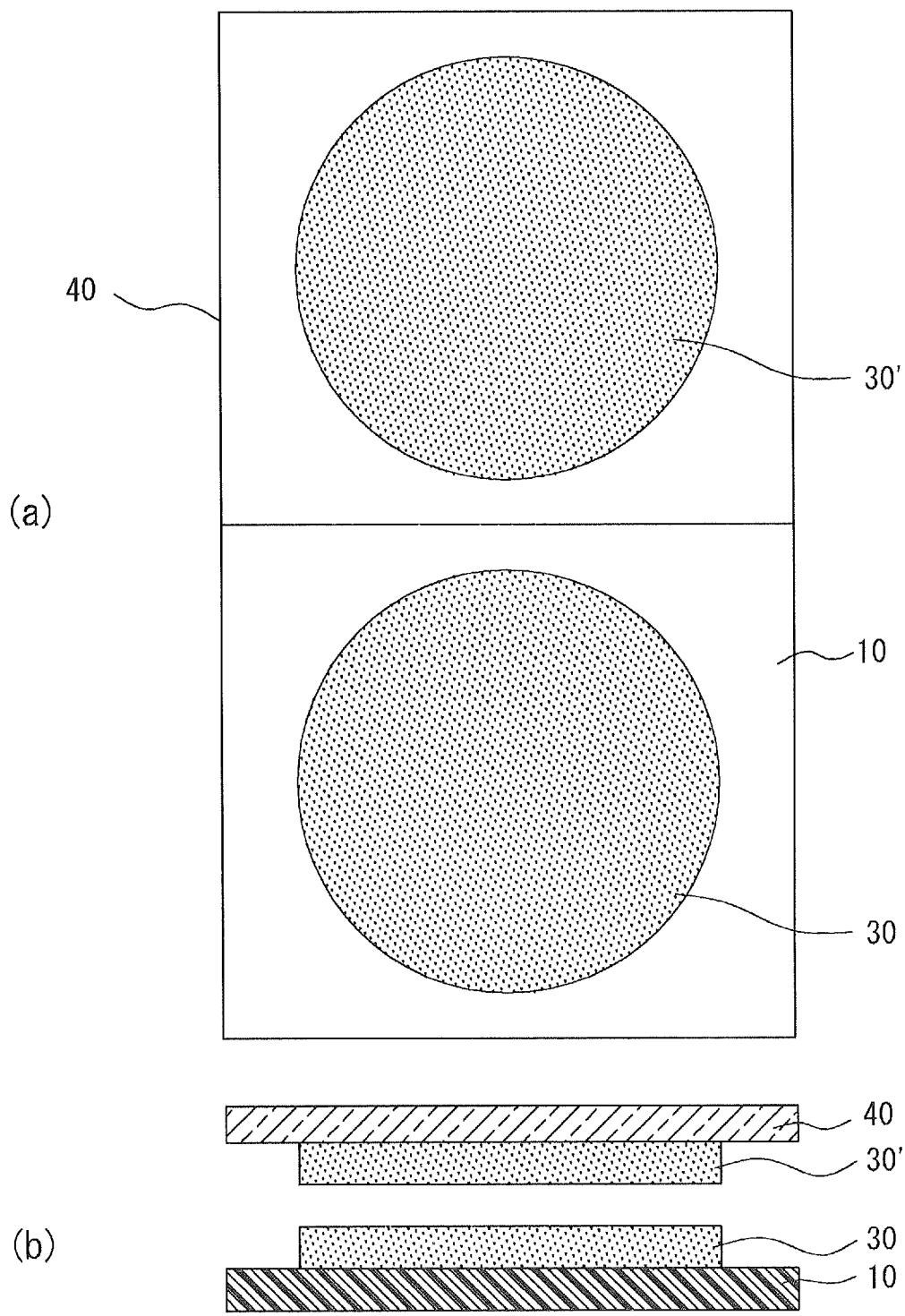
FIG. 3 is a drawing where 3(*a*) is a developed view and 3(*b*) is a cross sectional view, showing one example of the microorganism culture sheet according to the present invention; showing a state where a culture layer is formed on the base sheet, and a specified component layer is formed on the cover sheet.

EXPLANATION OF THE REFERENCE NUMBERS 10 base sheet
20 frame layer
30 culture layer
30' specified component layer
40 cover sheet
50 adhesive layer
60 double sided adhesive tape

PREFERRED MODE FOR CARRYING OUT THE INVENTION

Below, the present invention will be explained in detail with reference to specific embodiments; however, the present invention is not in any way limited by these embodiments, and the present invention may be additionally carried out with appropriate modifications within the scope of the objective of the present invention.
[Microorganism Culture Sheet]

The microorganism culture sheet of the present invention is a microorganism culture sheet having a base sheet, a culture layer formed on top of the base sheet, and a cover sheet that covers the culture layer, and the culture layer is pattern-formed of an application liquid comprising a polyvinylpyrrolidone, and at least one selected from the group consisting of a gelling agent, a nutrient component, a color indicator, a selective agent, and a substrate.

The microorganism culture sheet of the present invention preferably has a frame layer consisting of a hydrophobic resin formed at the outer boundary of the culture layer. Further, the gelling agent is preferably a high polymer polysaccharide. Furthermore, the content of the gelling agent in the application liquid is preferably 100 to 600 parts by weight, with respect to 100 parts by weight of the polyvinylpyrrolidone. Moreover, the base sheet and/or the cover sheet preferably consist of a transparent plastic sheet, and the cover sheet may be provided fixed to the base sheet.

(1) Constitution of the Microorganism Culture Sheet

One example of a suitable mode of the microorganism culture sheet of the present invention is shown in FIGS. 1(a) and 1(b). FIG. 1(a) is a top view, and FIG. 1(b) is a cross sectional view along A-A' of FIG. 1(a).

FIG. 1 shows the state where the culture layer (30) is formed approximately in the center of the square base sheet (10), and further, the square cover sheet (40) is provided so as to cover the culture layer (30). The present invention is characterized in the point that the culture layer (30) is pattern-formed on the base sheet (10), and as shown in the cross sectional view of FIG. 2(a), the base sheet (10) may also be a multilayer sheet consisting of the base sheet (11) and the base sheet (13), and furthermore, it may also be a multilayer sheet where a layer other than plastic is laminated. Further, as shown in FIG. 2(b), the culture layer (30) may also have a multilayer constitution of 2 or more layers.

The shape of the culture layer (30) prepared by pattern-forming is not limited to the circular form shown in FIG. 1, and may also be a square, rectangle, other polygon, or amorphous.

In the microorganism culture sheet of the present invention, as shown in the developed view of FIG. 3(a), the culture layer (30) and a specified component layer (30') which comprises a binder component, a nutrient component or other components, may respectively be formed on both the base sheet (10) and the cover sheet (40). For example, in the case that both the culture layer (30) and the specified component layer (30') include a gelling agent, the culture layer (30) on top of the base sheet and the specified component layer (30') provided on the cover sheet (40) are disposed to face each other, thus, for example, after inoculating the test liquid onto the culture layer (30) on top of the base sheet (10), and covering the culture layer (30) with the cover sheet (40), water absorption of the test liquid into the culture layer (30) and the specified component layer (30') occurs, and it is possible to observe microorganisms in both the culture layer (30) and the specified component layer (30'). Further, if an indicator is included in the culture layer (30), during the sterilization process, coloring may be notable, and in this case, by including the indicator in the specified component layer (30'), it is possible to prevent coloring at the time of the sterilization process. Further, FIG. 3(b) is a side cross sectional view.

Figure 4:
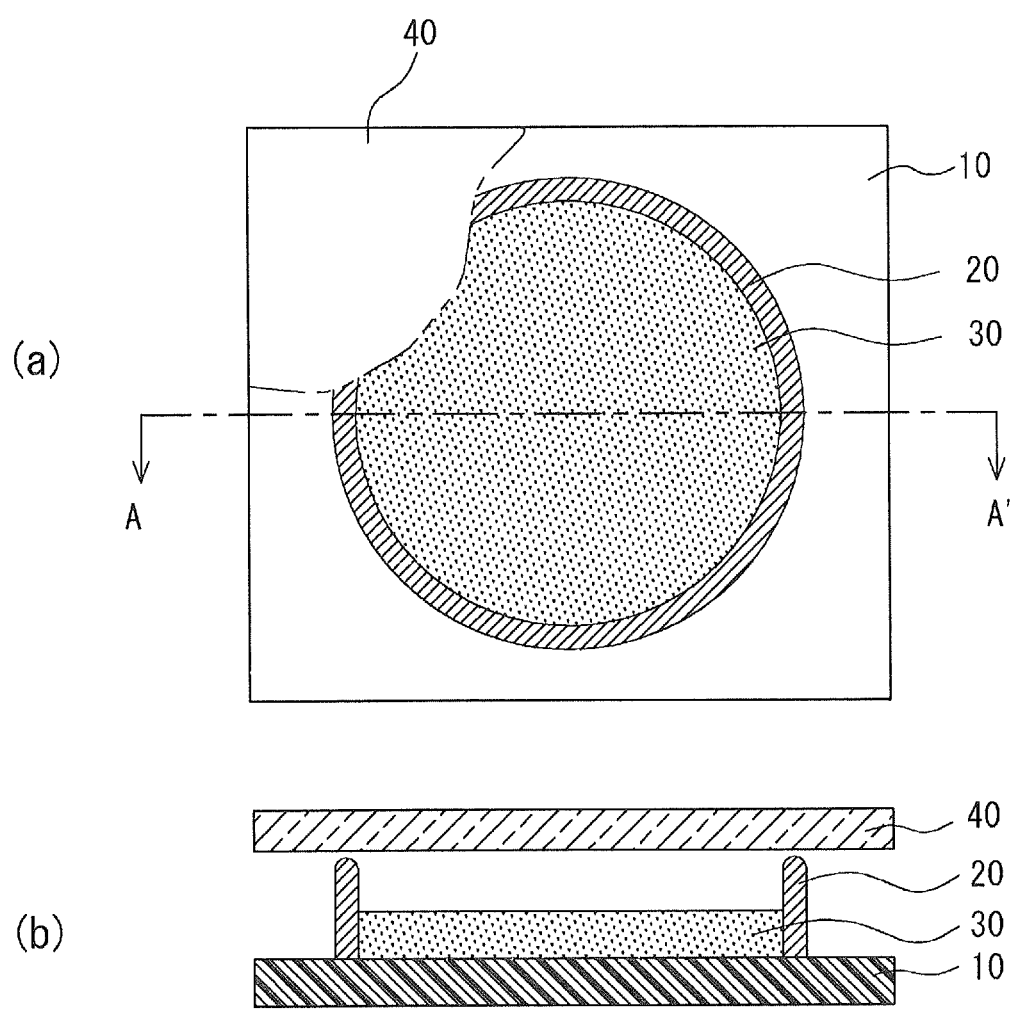
FIG. 4 is a drawing where 4(*a*) is a top view and 4(*b*) is a cross sectional view, showing one example of the microorganism culture sheet according to the present invention, showing a state where the culture layer and the frame layer are formed on top of the base sheet.
Figure 5:
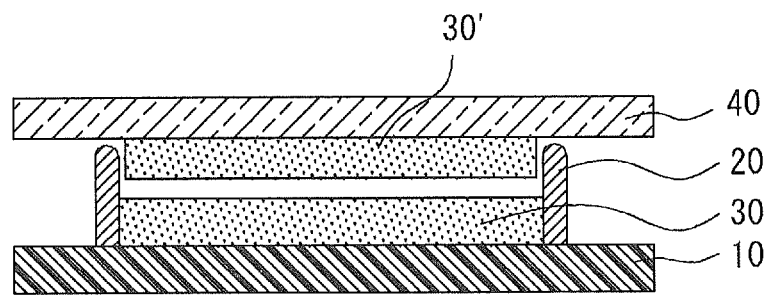
FIG. 5 is a cross sectional view showing one example of the microorganism culture sheet according to the present invention; showing a state where the culture layer and the frame layer are formed on top of the base sheet, and a specified component layer is formed on the cover sheet so as to face the inner side of the frame layer.

Further, in the microorganism culture sheet of the present invention, as shown in the top view of FIG. 4(a) and the A-A' line cross sectional view of FIG. 4(b), the culture layer (30) is formed approximately in the center of the base sheet (10), and the frame layer (20) with a circular shape may be formed at the outer boundary of the culture layer. The frame layer (20) can more securely limit the water absorption area of the test liquid inoculated to the culture layer (30). Further, the shape of the frame layer (20) is not limited to a circular shape, and may be any of square, elliptical, polygonal, amorphous or the like, but the frame layer is preferably formed so as to ensure that the water absorption area of the test liquid inoculated onto the culture layer (30) is in a predetermined area. Further, in this mode, as shown in the cross sectional view of FIG. 5, a specified component layer (30') is further formed on the cover sheet (40) so as to face the culture layer (30) on top of the base sheet (10).

Figure 6:
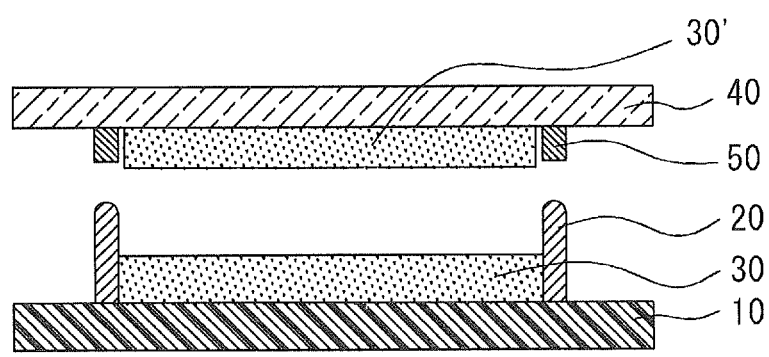
FIG. 6 is a cross sectional view showing one example of the microorganism culture sheet according to the present invention; showing a state where the culture layer and the frame layer are formed on the base sheet, and a specified component layer is formed on the cover sheet so as to face the inner side of the frame layer, and further, an adhesive layer is formed on the cover sheet so as to face the frame layer.

Furthermore, as shown in FIG. 6, an adhesive layer (50) may be formed on the cover sheet (40), so as to face the frame layer (20). By adhering the frame layer (20) and the adhesive layer (50), drying and contamination of the culture layer (30) can be more effectively prevented.

Figure 7:
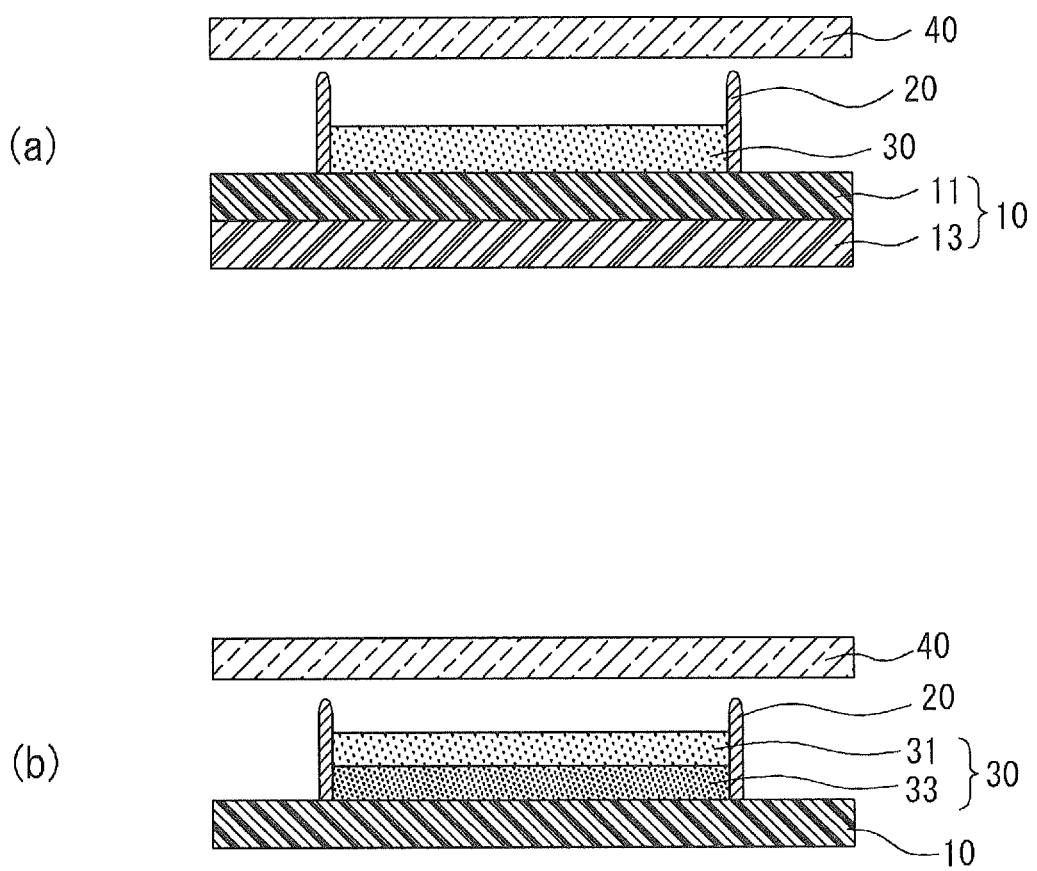
FIG. 7 is a cross sectional view of one example of the microorganism culture sheet according to the present invention where the frame layer is formed on top of the base sheet, where 7(*a*) is a drawing showing a state wherein the base sheet has a multilayer structure, and 7(*b*) is a drawing showing a state where the culture layer has a multilayer structure.

The microorganism culture sheet of the present invention, as shown in the cross sectional view of FIG. 7(*a*), even when the frame layer (20) consisting of a hydrophobic resin is formed on the surface of the base sheet (10), the base sheet (10) may be in the form of a multilayer sheet consisting the two layers of a base sheet (11) and a base sheet (13), and may also be a multilayer sheet where a layer other than plastic is laminated. Further, as shown in the cross sectional view of FIG. 7(*b*), even in the case that the frame layer (20) consisting of a hydrophobic resin is formed on the surface of the base sheet (10), the culture layer (30) may have a multilayer constitution of 2 or more layers.

Figure 8:
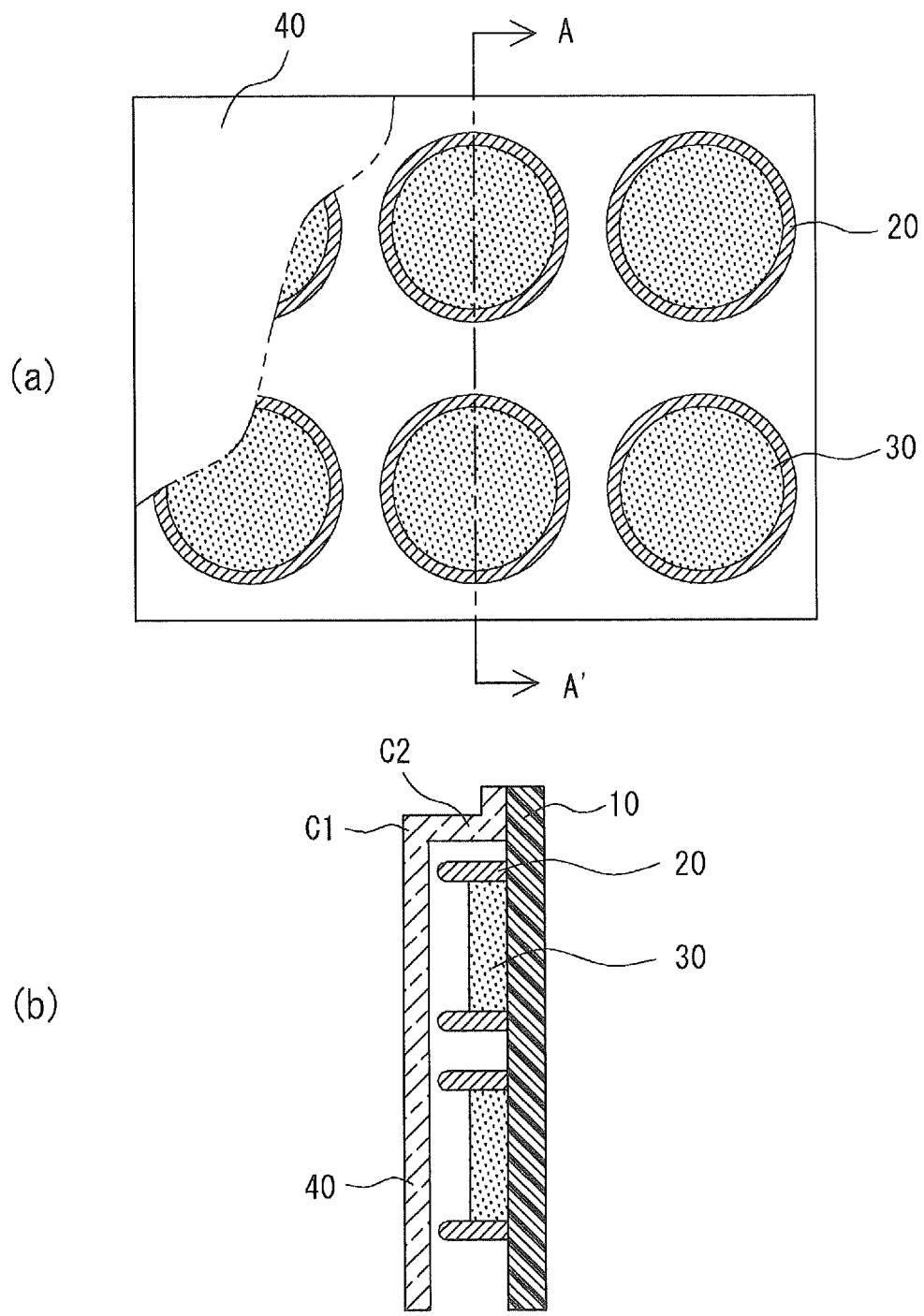
FIG. 8 is a drawing showing one example of the microorganism culture sheet according to the present invention where 8(a) is a top view and 8(b) is a cross sectional view, showing a state where a plurality of culture layers, surrounded by the frame layer at their outer boundary, are formed on top of the base sheet, where the cover sheet is provided fixed to the base sheet.

Further, there may also be a plurality of the culture layers (30) on top of the base sheet (10). FIGS. 8(*a*) and 8(*b*) show a form with a plurality of culture layers (30), frame layers (20) consisting of a hydrophobic resin with a convex form surrounding their outer boundaries, and a cover sheet (40) that covers the culture layers (30) provided fixed on the distal end of the base sheet (10). FIG. 8(*a*) is a top view, and FIG. 8(*b*) is an A-A' cross sectional view of FIG. 8(*a*). In FIG. 8, the cover sheet (40) has a form with two angled portions (C1 and C2) formed thereon so that it can cover the culture layer (30), and further be adhered to the top portion of the frame layer (20). Further, while this differs from FIG. 8, a specified component layer (30') may also be formed on the cover sheet (40) so as to face the culture layer (30) formed on top of the base sheet (10).

The diameter of the equivalent circle of the culture layer (30) is preferably from 20 to 80 mm, and more preferably from 30 to 70 mm. The test liquid instilled onto the microorganism culture sheet is generally 1 ml, and within the above range, sufficient water absorption of the test liquid can occur.

Further, generally, the height of the frame layer (20) is prepared to be 100 to 1200 μm higher, preferably 200 to 1000 μm higher, more preferably 300 to 800 μm higher than height of the culture layer. If within the above range, after inoculating the test liquid onto the culture layer (30), when covering with the cover sheet (40), leaking of the test liquid can be more securely prevented, and further, it is possible to quickly spread the test liquid to the frame layer (20) without producing air gaps between the culture layer (30) and the cover sheet (40). Further, even after water absorption of the test liquid at the culture layer, it is possible to preserve the adhesion between the culture layer (30) and the cover sheet (40). It is possible to immediately cover with the cover sheet (40) without waiting for the water absorption by the culture layer of the test liquid after inoculation, thus the operational efficiency at the time of inoculation can be improved.

The width of the frame layer is not limited to a uniform width, but the narrowest portion preferably has a width of 0.5 to 5.0 mm, preferably from 1.0 to 3.0 mm. If within the above range, even if the culture layer swells with water absorption, there is no concern that the form of the frame layer will collapse, and the test liquid will spread over the prescribed region.

Further, the frame layer may also be single, or it may be a frame layer consisting of a double frame where a further frame layer is formed outside of the above frame layer.

(2) Base Sheet

In the microorganism culture sheet of the present invention, an application liquid comprising a polyvinylpyrrolidone, and at least one selected from the group consisting of a gelling agent, a nutrient component, a color indicator, a selective agent, and a substrate, is pattern-formed on top of a base sheet, and thus the base sheet must have solvent resistance and suitability for printing. Further, as a microorganism culture sheet, it is required to have water resistance, and when the culture layer is formed, it is required to have heat resistance to resist the heating process. The base sheet may be a single layer, or may be a laminate sheet of two or more layers.

In the case that the base sheet is a single layer, for example, a plastic sheet such as polyester, polyethylene, polypropylene, polystyrene, polycarbonate, polyvinyl chloride and the like can be suitably used. Because of these plastic sheets, the transparency is excellent, thus it is also possible to observe the microorganism colonies with the transmitted light from the base sheet, and the visibility can be improved. However, it is also possible to use plastic sheets showing a white color due to foaming, or any of those which have been colored. For bacterial cultivation, the plastic sheets are not limited to those which are transparent, and there may be cases where the bred colonies are easy to count by coloring, and the plastic sheets can be appropriately selected in consideration of this.

Further, as a laminate sheet, a laminate of two or more of the above plastic sheets can be mentioned as an example. Further, a laminate sheet where a paper base material is laminated to the above mentioned plastic sheet, or a laminate sheet where a synthetic resin is coated onto a paper base material and the like can be suitably used. As such a laminate sheet, for example, a laminate sheet of a polyethylene film and a paper base material can be mentioned as an example.

Furthermore, a synthetic paper with a synthetic resin as the main material can also be used as the base sheet. As such a synthetic paper, one with the trade name "Yupo" by the Yupo Corporation, and "Crisper" by Toyobo Co. Ltd., can be mentioned as examples.

The base sheet used in the present invention may be subjected in advance to a surface treatment on the side where the culture layer is pattern-formed in order to increase the adhesion to the culture layer. As such a surface treatment, there is for example a corona discharge treatment, an ozone treatment, low temperature plasma treatment using oxygen gas or nitrogen gas or the like, glow discharge treatment, oxidation treatment by treating with a chemical or the like, and other such pretreatments.

Further, the base sheet used in the present invention may be subjected to a surface treatment by coating with an anchor coating agent. As such an anchor coating agent, an isocyanate type (urethane type), polyethyleneimine type, polybutadiene type, organotitanium type, and other types of anchor coating agents can be mentioned as examples. More preferable are those having as the main ingredient, for example, multifunctional isocyanates such as aromatic polyisocyanates such as tolylenediisocyanate, diphenylmethanediisocyanate, polymethylenepolyphenylpolyisocyanate and the like; or aliphatic polyisocyanates such as hexamethylenediisocyanate, xylylenediisocyanate and the like; polyether polyols, polyester polyols, polyacrylate polyols and other polyetherpolyurethane type resins obtained by reacting with a hydroxyl base-containing compound, polyester polyurethane resins, and polyacrylate polyurethane resins.

The base sheet is preferably flat without curls or the like, and its thickness is not particularly limited, but is usually 25 to 1500 μm, more preferably 50 to 500 μm.

(3) Culture Layer

In the microorganism culture sheet of the present invention, the culture layer provided on top of the base sheet is pattern-formed of an application liquid comprising polyvinylpyrrolidone and at least one selected from the group consisting of a gelling agent, a nutrient component, a color indicator, a selective agent and a substrate, and the polyvinylpyrrolidone is an essential component of the application liquid.

(i) Polyvinylpyrrolidone

In the microorganism culture sheet of the present invention, the polyvinylpyrrolidone is an essential component of the application liquid, and has the role of adjusting the viscosity of the application liquid. The polyvinylpyrrolidone makes it possible to easily adjust the viscosity by adjusting the concentration in the solvent, thus it is possible to uniformly disperse at least one selected from the group consisting of a gelling agent, nutrient component, color indicator, selective agent and a substrate, and further, it becomes possible to pattern-form only the necessary portion, and no waste of the costly material arises. However, when the solvent is removed after pattern-forming, the film-forming property of the polyvinylpyrrolidone is high, thus, it is possible to form a film incorporating the gelling agent and the nutrient component. Further, it has a favorable adhesiveness to the base material, thus it is possible to form the culture layer without using an adhesive, and thus there is no concern of an adhesive agent component exerting an effect on the development of the microorganisms, as in the microorganism culture sheet of the prior art or the like.

(ii) Gelling Agent

In the microorganism culture sheet of the present invention, a gelling agent may be included in the application liquid. A culture layer formed by pattern-forming the application liquid comprising the gelling agent thickens or gels when the test liquid is inoculated, thus it reaches a favorable viscosity for the cultivation of germs. Further, it can suppress the drying of the culture layer during cultivation, by adhering to the cover sheet after thickening.

As such a gelling agent, a high polymer polysaccharide can be suitably used, and carrageenan, guar gum, xanthan gum, hydroxyethylcellulose, carboxymethylcellulose, locust bean gum, algin and the like can be mentioned as examples. These high polymer polysaccharides thicken or gel with water from the instilling of the test liquid, thus the growth of germs becomes favorable, and further, because the transparency is high, the visibility of the colonies is excellent, and furthermore, because of adhesion to the cover sheet by the thickening, it is possible to suppress drying during cultivation. In the microorganism culture sheet of the present invention, among these, guar gum can be particularly suitably used. Guar gum exhibits a very high viscosity at low concentrations, thus it can produce an environment suitable for growth of germs in low amounts. Further, guar gum is manufactured from the albumen of the seed of guar, which is an annual pulse plant.

(iii) Nutrient Component

In the microorganism culture sheet of the present invention, a nutrient component may be included in the application liquid. As the nutrient component, for example, for ordinary microorganism testing, a yeast extract•peptone•glucose mixture, a meat extract•peptone mixture, a peptone•soy peptone•glucose mixture and the like, these mixed with dipostassium phosphate and/or sodium chloride may be used. For E. coli•coliform testing, sodium deoxycholate•peptone•ferric ammonium citrate•sodium chloride•dipostassium phosphate•lactose•peptone •dipostassium phosphate and the like may be used. For Staphylococcus, a meat extract•peptone•sodium chloride•mannitol•egg yolk mixture, or a peptone•meat extract•yeast extract•sodium pyruvate•glycine•lithium chloride•tellurous acid egg yolk mixture may be used. For Vibrio, a yeast extract•peptone•sucrose•sodium thiosulfate•sodium citrate•sodium cholate•ferric citrate•sodium chloride•bovine bile and the like may be used. For Enterococci, bovine brain extract•heart extract•peptone•glucose•dipostassium phosphate•sodium nitride and the like may be used. For fungi, a peptone•glucose mixutre, yeast extract•glucose mixture, potato extract•glucose mixture and the like may be used. In the microorganism culture sheet of the present invention, among these, one type or more nutrient component is selected according to the microorganism to be cultivated, and mixtures may be used. Further, if a nutrient component is not included in the culture layer, or if the nutrient component is insufficient, the nutrient component may be added to the test liquid to grow the microorganisms.

(iv) Other Components Such as Color Indicator, Selective Agent, Substrate and the Like In the microorganism culture sheet of the present invention, other components such as a color indicator, selective agent, substrate may be included in the application liquid.

The color indicator colors a colony by becoming colored by reacting with specific substances produced by the metabolism of the microorganisms grown in the cultivation process, marking a pH change, or reacting with an enzyme or the like, and thus has the effect of making it very easy to count the colonies. As such a color indicator, specifically, there are tetrazolium salts such as triphenyl tetrazolium chloride (below referred to as TTC), p-tolyltetrazolium red, tetrazolium violet, tetrazolium blue and the like, neutral red mixtures, and pH indicators such as phenol red, bromothymol blue, thymol blue mixtures and the like.

In the application liquid, a selective agent may be included to suppress the growth of microorganisms other than those to be detected. As such a selective agent, antibiotic agents such as antibiotics and synthetic antimicrobial agents, dyes, surfactants, inorganic salts and the like may be used. As an antibiotic, methicillin, cefmetazole, cefixime, ceftazidime, cefsulodin, bacitracin, polymyxin B, rifampicin, novobiocin, colistin, lincomycin, chloramphenicol, tetracycline, streptomycin and the like may be mentioned as examples, and as synthetic antimicrobial agents, sulfa drugs, nalidixic acid, olaquindox and the like may be mentioned as examples. Further, as dyes, crystal violet, brilliant green, malachite green, and methylene blue, and the like, which have bacteriostatic or bactericidal action, may be mentioned as examples. Further, as surfactants, Tergitol 7, dodecyl sulfate salts, lauryl sulfate salts and the like may be mentioned as examples. Further, as the inorganic salts, selenite, tellurite, sulfite, sodium nitride, lithium chloride, oxalate, high concentration sodium chloride and the like may be mentioned as examples. Other than these, taurocholate, glycine, bile powder, bile salt, deoxycholate and the like may be used.

These components may be added as powders, or after dissolving in a solvent, for example, they can be mixed into the alcohol solution of the polyvinylpyrrolidone, as the application liquid. Further, depending on the type of color indicator, coloring may be notable in the sterilization process, thus it is possible to carry out coloring using a color indicator included in the test liquid without including it in the culture layer.

Further, in the microorganism culture sheet of the present invention, the culture layer is not limited to being formed of a single layer, and it may have a multilayer constitution of 2 or more layers. For example, a first culture layer formed with an application liquid comprising a polyvinylpyrrolidone solution (i) with a gelling agent (ii), and on top of this, a second culture layer formed with an application liquid comprising a polyvinylpyrrolidone (i) solution with a gelling agent (ii) and a nutrient component (iii), may be used as the culture layer in the present invention. Further, the gelling agent may be included only in the first layer, and the first culture layer formed with an application liquid comprising a polyvinylpyrrolidone solution (i) with a gelling agent (ii), and on top of this, a second culture layer formed with an application liquid comprising a polyvinylpyrrolidone solution (i) with a nutrient component (iii), may be used as the culture layer in the present invention.

Further, if a reaction would occur in a mixture due to a combination of the color indicator and the selective agent, these can be included in different layers to prevent a reactive mixture. Further, by forming the uppermost layer with the color indicator, it is possible to improve the visibility of the colonies. Accordingly, for example, in the case of including components A and B which form a reactive mixture in the nutrient component, the culture layer may be laminated of two layers which are a first culture layer of a polyvinylpyrrolidone solution (i)+gelling agent (ii)+nutrient component (iii) from which the component A is removed, and a second culture layer of a polyvinylpyrrolidone solution (i)+gelling agent (ii)+colorant (iv)+nutrient component (iii) from which the component B is removed, or further, may be a culture layer where three layers are laminated in order: a first culture layer of a polyvinylpyrrolidone solution (i)+gelling agent (ii)+nutrient component (iii) from which the component A is removed, a second culture layer of a polyvinylpyrrolidone solution (i)+gelling agent (ii)+nutrient component (iii) from which the component B is removed, and a third culture layer consisting of a polyvinylpyrrolidone solution (i)+gelling agent (ii)+color indicator (iv). Further, a reactive mixture is not limited to the case of being occurring in the nutrient component, and may also arise in relation to the selective agent or the color indicator. In any case, by dividing the components A and B into separate layers, a reactive mixture can be prevented.

Moreover, in the present invention, in the case that the culture layer is constituted of multiple layers, any of the culture layers constituting the multilayer structure may be pattern-formed with an application liquid comprising polyvinylpyrrolidone and at least one selected from the group consisting of a gelling agent, a nutrient component, a color indicator, a selective agent and a substrate, and the other composition of the other layers is not limited to the above, and the pattern-forming method is irrelevant.

(v) Pattern-Forming

The culture layer in the microorganism culture sheet of the present invention is pattern-formed with an application liquid on top of the base sheet. In the microorganism culture sheet of the present invention, the culture layer is pattern-formed, thus after instilling the test liquid, by immediately covering with the cover sheet, the test liquid naturally spreads over a predetermined area, and the operability is excellent. In the present invention, "pattern-forming" refers to printing, applying, coating, spraying or the like, of the application liquid in a predetermined form on top of the base sheet, and the method is not particularly limited. Accordingly, for the pattern-forming, screen printing, gravure printing, relief printing, transfer printing, flexographic printing, other printing, applying by a dispenser or inkjet or the like, coating by bar coating using a bar or the like or knife coating, die coating or the like, spraying with a spray method or the like, and other methods may be used.

(4) Cover Sheet

In the microorganism culture sheet of the present invention, the cover sheet is preferably provided fixed to the base sheet. The cover sheet, in addition to preventing contamination of the culture by airborne microbes, also prevents evaporation of the moisture of the culture layer. The cover sheet at the same time as being waterproof and impermeable to water vapor, is also preferably transparent to make it possible to observe and count the colonies through the cover sheet after the cultivation of the microorganisms, and for example a plastic sheet of polyolefins such as polyethylene, polypropylene and the like, polyester, polyamide, polystyrene, polycarbonate, polyvinylchloride and the like, as mentioned for the base sheet, can be used. In the microorganism culture sheet of the present invention, if the base sheet and the cover film are transparent, observation is possible with the projected light from the rear face of the microorganism culture sheet, and further, observation is possible with incident light from the side face. Namely, it is possible to observe and count the colonies from the cover sheet side and from the base sheet side, thus the range of available choices for selecting the observation method and counting method become wider. Further, considering the operability of opening and closing the cover sheet, a polyester film and a polyolefin film are particularly preferable.

Further, the cover sheet may be surface treated by corona discharge treatment or the like as disclosed in the paragraph concerning the base sheet. Further, the cover sheet, depending on the type of microorganism cultured, preferably has a suitable gas permeability, mainly oxygen permeability, or oxygen impermeability, and may be selected in consideration of this point.

When lifting the cover sheet from the base sheet for inoculating the test liquid, it is preferable to ensure an appropriate degree of flexibility. Accordingly, the thickness of the cover sheet, is preferably from 10 to 200 µm, more preferably 20 to 70 µm. Further, the cover sheet may have any shape, but in order to prevent entry of contaminant germs, it is required to have a size greater than the culture layer which can cover the culture layer.

In the microorganism culture sheet of the present invention, the cover sheet may also have a specified component layer made by applying a specified component solution comprising at least one selected from the group consisting of a gelling agent, nutrient component, color indicator, selective agent, and substrate in a solution of a binder resin or in a liquid where a binder resin is dispersed, and positioned to face the culture layer formed on the base sheet. As mentioned above, in the microorganism culture sheet of the present invention, the culture layer formed on the base sheet is pattern-formed with an application liquid comprising a polyvinylpyrrolidone, and a gelling agent or the like, and may be in a form which does not include a color indicator. In such a case, cultivation may be carried out with a color indicator added to the test liquid, but by forming on the cover sheet a specified component layer by pattern-forming a specified component liquid consisting of a binder solution and a color indicator such as a TTC reagent or the like, it is possible to eliminate the work of adding the color reagent to the test liquid, and further visibility can be ensured by the adhesiveness of the binder. Further, as the binder, it is possible to use a water soluble resin such as polyethyleneimine or polyethyeneoxide, or an acrylate type polymer, or an alcohol soluble resin or the like. Further, provided that it is possible to exert the functions of the components included in the specified component layer, it is also possible to use a solution or a dispersion of a hydrophobic binder.

Further, the specified component layer of the cover sheet should be present at least at a position facing the culture layer of the base sheet, and it may be applied over the entire face of the cover sheet. The binder solution is inexpensive, and the color indicator is used in small amounts. Further, the specified component layer may also include a gelling agent. Further, the specified component layer is not limited to the case of a single layer, and may be a multilayer of two or more layers.

For forming the above specified component layer, it is possible to use screen printing, gravure printing, relief printing, transfer printing, flexographic printing, other printing, application by a dispenser or inkjet or the like, coating such as bar coating by coating with a bar or the like, knife coating, die coating or the like, spraying such as a spraying method, or other coating methods. Further, it may be patternformed.

Further, in the microorganism culture sheet of the present invention, the cover sheet is not limited to being provided fixed to the microorganism culture sheet. Accordingly, it is possible to use a separately prepared cover sheet, to cover the culture layer after inoculating the test liquid. However, in the form were the cover sheet is provided fixed to the base sheet in advance, the operability is good.

Further, in the case that a grid print pattern is not printed on the base sheet, a grid print pattern may be printed in advance on the cover sheet with an ink which is water insoluble and does not exert any influence on the growth of the microorganisms. The printing process of the printing, in the same way as for the base sheet, is preferably done with gravure printing or the like, for the point of a wide range of selection of the colorant, resin, solvent and the like. It is suitable for the size of the grid to be squares on the order of 1 cm.

(5) Frame Layer

In the microorganism culture sheet of the present invention, it is preferable to form a frame layer consisting of a hydrophobic resin at the outer boundary of the culture layer. When the frame layer is formed, when inoculating the test liquid on the culture layer and covering with the cover sheet, because the test liquid quickly spreads to the frame layer, it is possible to cover with the cover sheet without waiting for the water absorption of the test liquid by the culture layer, and the inoculation operation can be carried out in a short time. Further, the frame layer can securely prevent the leaking of the test liquid, improving the operability at the time of the inoculation. In the case that a gelling agent is included in the culture layer, water absorption of the test liquid occurs at the culture layer which is inside of the frame layer, and the gelling agent thickens, which can prevent drying of the culture layer by the adhesion between the culture layer and the cover sheet. Further, even if a gelling agent is not included in the culture layer, the polyvinylpyrrolidone dissolves and thickens, thus it is possible to prevent drying of the culture layer by the adhesion between the culture layer and the cover sheet. When there is excellent adhesion between the culture layer and the cover sheet, there is no need to form a layer or the like for colony formation on the cover sheet, and excellent visibility of the colonies can be ensured.

The width of the frame layer is not limited to a uniform width, and the narrowest portion preferably has a width of 0.5 to 5.0 mm, more preferably 1.0 to 3.0 mm. Within the above range, even in the case that the culture layer absorbs water and swells, the form of the frame layer does not collapse, and the test liquid can spread within a predetermined range.

In the microorganism culture sheet of the present invention, the height of the frame layer formed on top of the base sheet is prepared to be 100 to 1200 $\mu$m higher, preferably 200 to 1000 $\mu$m higher, and particularly preferably 300 to 800 $\mu$m higher than the height of the culture layer. If it is less than 100 $\mu$m, it is not possible to suppress the spreading of the test liquid after it has spread, and leakage arises. On the other hand, if it exceeds 1200 $\mu$m, it is difficult to ensure the adhesion with the cover sheet because of the generation of excessive air gaps between the culture layer and the cover sheet when the test liquid is inoculated, and the culture layer can easily dry during the cultivation, or even in the case that the cover sheet and the culture layer are temporarily adhered, after water absorption of the test liquid at the culture layer, the cover sheet peels from the culture layer due to an excess of air, which may lead to drying of the culture layer. If within the above range, the test liquid can spread over the entire surface of the culture layer while water absorption occurs, and leakage can be more securely prevented, and the adhesion with the cover sheet can be ensured.

Further, the above frame layer is formed on top of the base sheet. If the frame layer is formed on top of the culture layer, when the culture layer swells and gels by water absorption of the test liquid, there is concern of collapse, thus it is preferably formed directly on top of the base sheet. If the frame layer is formed on top of the base sheet, the working operability and stability are excellent.

In the microorganism culture sheet of the present invention, the frame layer is formed of a hydrophobic resin, thus it does not absorb water or dissolve, and it is possible to prevent leaking of the test liquid. As the hydrophobic resin for forming the frame layer, there are no particular limitations, and a UV curable resin, hot melt resin, thermally foamed ink and UV foaming agent and the like can be suitably used, and these may be colored.

As UV curable resins, for the radical type, acrylates and unsaturated polyesters; and for the cationic type, epoxyacrylates, oxetanes, and vinyl ethers and the like can be mentioned as examples, but it is not limited to these.

Further, as hot melt resins, those with a softening point temperature of 120° C. or less, more preferably 100° C. or less, can be suitably used. When exceeding 120° C., the base sheet may curl. As the hot melt resins which can be suitably used in the present invention, urethanes, polyamides, polyolefins, polyesters, ethylene vinyl acetates, and synthetic rubbers such as styrene-butadiene rubbers and urethane rubbers and the like can be mentioned, but they are not limited to this.

As the hydrophobic resin, thermally foamed inks and UV foaming agents and the like may be suitably used. For example, as the binder, polyurethane resins, polyamide resins, polyvinyl chloride resins, polyacrylate resins, polyester resins, and polyolefin resins such as chlorinated polypropylene and the like, and further, rubbers such as chlorinated rubber and cyclized rubber and the like may be used. It is even more preferable for these inks to be water repellent, rather than only hydrophobic, and from this point, inks where a silicone or wax has been added to the above mentioned resins are more preferable. In particular, the hydrophobic resin used for the frame layer, at the same time as being hydrophobic/water repellent, has to have a thick coating thickness, and it is effective to add a publicly known foaming agent or the like to the above resin, for use as a foamed ink. As such a UV foaming ink, a UV curable foaming ink comprising a foaming agent such as an inorganic foaming agent, organic foaming agent, liquid foaming agent or the like, in a UV curable ink consisting of a reactive diluent such as at least an acrylate reactive diluent or a methacrylate reactive diluent; a photopolymerizable oligomer such as urethane acrylate photopolymerizable oligomer, polyesteracrylate photopolymerizable oligomer, epoxyacrylate photopolymerizable oligomer, acrylic photopolymerizable oligomer, a special photopolymerizable oligomer or the like; and a photopolymerization initiator.

Further, an antifoaming agent, polymerization inhibitor, pigment dispersant or the like may be added to the above hydrophobic resin as an additive. Further, a usually used coloring pigment may be added in a range of less than 15 wt %; if exceeding 15 wt %, there is concern that foaming would be inhibited, which is not preferable.

In the present invention, as the hydrophobic resin, those mentioned above can be suitably used, however, UV curable resins and hot melt resins are particularly favorable. The reason for this is that the formation of the frame layer requires pattern-forming with a predetermined height, and these two types of resins are easy to form-process by applying with a dispenser or the like in a non-solvent state, and after this, can be pattern-formed merely by readily curing by photoirradiation or cooling.

Further, in the microorganism culture sheet of the present invention, the frame layer may be formed by adhering a cutout of a hydrophobic material at the outer boundary of the culture layer. Furthermore, there is also a method of using an embossed article as the base sheet. For example, for an embossed article where a protrusion is formed at the base sheet as the form of the frame layer, the culture layer may be formed inside the above protrusion, on the other hand, it is also possible to form a recessed portion at the location for forming the culture layer, and to use the remaining portion which is formed to protrude from this as the frame layer.

Furthermore, it is also possible to use a method of using a thick hydrophobic base material as the base sheet, and removing a recessed form portion which forms the culture layer, and the remaining portion forming the frame layer; or to form a protrusion for the shape of the frame layer, and to form the culture layer inside the protrusion, and to use the protrusion as the frame layer. However, it is not limited to these.

(6) Adhesive Layer

In the microorganism culture sheet of the present invention, it is possible to form an adhesive layer at the base sheet and the cover sheet. Such an adhesive layer fixes a cover sheet covering the culture layer, and is provided with the objective of preventing the moisture evaporation and contamination of the culture layer, and any type of adhesive may be used as long as it can seal the base sheet. Considering the workability, it is preferable to use an adhesive having a weak adhesive force such that it is possible to re-adhere the base sheet and the cover sheet. For example, a rubber adhesive or acrylic adhesive is preferable, and a re-detachable type or a micro-adhesive type acrylic adhesive is particularly preferably used. Specifically, one can be used where rosin, xylene resin, phenol resin or the like is added as an adhesion imparting agent to a polymer copolymerized from 2 to 15 parts by weight of a monomer having a functional group such as a carboxyl group, a hydroxyl group, an amino group or the like, with respect to 100 parts by weight of an acrylate with a carbon number of 2 to 12 such as a butylacrylate or 2-ethylhexylacrylate or the like, and crosslinked with a melamine, isocyanate, epoxy or the like. Further, the adhesive layer may have any shape, but it is preferably provided such that it can adhere the adhering portions of the base sheet and the cover sheet without any gaps.

The thickness of the adhesive layer is not particularly limited, but should be such that the cover sheet covers the culture layer formed on the base sheet, and further, to maintain the adhesion with the base sheet.

Further, the present invention is not limited to an adhesive layer for sealing the culture layer with the cover sheet, and it is also possible to use methods such as using a holding member, or providing a weight or the like.

(7) Grid Pattern Print Layer

In the microorganism culture sheet of the present invention, a grid pattern print layer may also be laminated. The grid pattern print is preferably a gravure print from the point of a wide range of selection of the colorant, resin, solvent and the like. It is suitable for the size of the grid to be squares on the order of 1 cm.

Such a grid pattern print layer, as mentioned above, may be formed on the base sheet or the cover sheet, but in the present invention, if a laminate sheet where a paper material is laminated to a plastic sheet is used as the base sheet, the grid pattern print layer may be formed on such a paper material.

(8) Microorganism Culture Kit

In the present invention, it is possible to make a microorganism culture kit by combining the above mentioned microorganism culture sheet and a test liquid comprising a specified component.

As described above, in the microorganism culture sheet of the present invention, the culture layer formed on top of the base sheet is a layer pattern-formed by printing, coating or the like with an application liquid comprising a polyvinylpyrrolidone and at least one selected from the group consisting of a gelling agent, a nutrient component, a color indicator, a selective agent, and a substrate, and in such a case, cultivation can be carried out by adding to the test liquid a component which is not included in the culture layer, from among the gelling agent, nutrient component, color indicator, selective agent and substrate. In particular, this is effective in the case of including a component which is easily deteriorated, discolored, decomposed or the like during a sterilization process or other processes.

As a microorganism culture sheet which can be used in such a microorganism culture kit, it is possible to use one where a specified component layer is formed on the above mentioned cover sheet. The components which are not included in the specified component layer or the culture layer formed on top of the base sheet can be added to the test liquid for cultivation.

(9) Manufacturing Method (i) Formation of the Culture Layer

Provided that for the microorganism culture sheet of the present invention, it is possible to form a culture layer which is pattern-formed on top of the base sheet with an application liquid comprising a polyvinylpyrrolidone and at least one selected from the group consisting of a gelling agent, a nutrient component, a color indicator, a selective agent and a substrate, its manufacturing method is irrelevant. Further, the pattern-forming method is also not particularly limited provided that it is possible to apply the application liquid onto the base sheet in a predetermined form, and may be the any of the above-mentioned methods of printing, application, coating, spraying or the like. Preferably, an application liquid comprising, in an alcohol solution of a polyvinylpyrrolidone, at least one selected from the group consisting of a gelling agent, nutrient component, color indicator, selective agent, and a substrate is prepared, and after pattern-forming the application liquid on top of the base sheet, the alcohol solution included in the above mentioned application liquid is removed to form the culture layer.

In the method of manufacturing the microorganism culture sheet of the present invention, it is preferable to use an alcohol solution of polyvinylpyrrolidone for reasons of adhesion between the base sheet and the culture layer, and the ease of pattern-forming. As the alcohol, an alcohol with a carbon number of 1 to 5 can be suitably used. For example, one of, or mixtures of two or more of methanol, ethanol, isopropyl alcohol, butanol and the like can be used. Among these, methanol, ethanol, and isopropyl alcohol are preferable. In the prior art, high boiling point solvents such as water and toluene were used for dissolving the nutrient component, however, for solvent removal, heating at a high temperature was necessary, and there was concern of incurring thermal decomposition of the base material or the components included in the culture layer. Further, it was necessary to use excessive thermal energy for the solvent removal, which was a cause of increased costs, and further, because the solvent elimination time was long, this was a cause of reduced production efficiency. In the present invention, by using polyvinylpyrrolidone, and using the above mentioned alcohol which has a low boiling point as the solvent, thermal denaturation of the components included in the application liquid and of the base material can be avoided, and the production efficiency can be increased. Further, it is possible to use a solvent where an auxiliary solvent such as chloroform or the like is mixed with the alcohol, within a scope which does not lose the above mentioned effects.

The polyvinylpyrrolidone is an essential component of the application liquid because, as mentioned above, by adjusting the concentration, it is possible to uniformly disperse at least one selected from the group consisting of a gelling agent, nutrient component, color indicator, selective agent and substrate, and moreover, the viscosity can be easily adjusted, thus it becomes possible to pattern-form with the obtained application liquid. Further, polyvinylpyrrolidone has excellent film-forming properties and adhesiveness with respect to the base sheet, thus it is possible to form the culture layer on the base sheet without using an adhesive, and it is possible to avoid growth inhibition of the microorganisms by the adhesive.

The proportion of alcohol to the polyvinylpyrrolidone is 100 to 10000 parts by weight of solvent with respect to 100 parts by weight of polyvinylpyrrolidone, and more preferably 300 to 2000 parts by weight, particularly preferably 900 to 1400 parts by weight. If exceeding 10000 parts by weight, the dispersibility of the gelling agent notably deteriorates, on the other hand, if lower than 100 parts by weight, the viscosity of the application liquid increases, and its applicability to pattern-forming is reduced.

In the microorganism culture sheet of the present invention, if it is possible to pattern-form the gelling agent constituting the application liquid, it is not necessary that it be dissolved in the above mentioned alcohol solution of polyvinylpyrrolidone. Accordingly, in the method of manufacturing the microorganism culture sheet of the present invention, the gelling agent can be added as a powder. In the case of adding as a powder, the average particle diameter of the gelling agent is 5 to 500 µm, preferably 10 to 200 µm. If the average particle size is within this range, the dispersibility is excellent. If exceeding 500 µm the dispersibility is degraded, and the suitability for pattern-forming may be lost. However, if dissolved in a solvent, it may be mixed with the polyvinylpyrrolidone alcohol solution in the application liquid.

The content of the gelling agent in the above mentioned application liquid is 100 to 600 parts by weight with respect to 100 parts by weight of the polyvinylpyrrolidone, more preferably 250 to 400 parts by weight. If the content of the gelling agent is within the above range, there is thickening or gelling due to the moisture when instilling the test liquid, and it is possible to obtain a viscosity favorable for the growth of germs. If less than 100 parts by weight, the viscosity of the culture layer may be insufficient, on the other hand, if exceeding 600 parts by weight, the culture layer may become hard, and the growth of germs may decline.

Further, because the polyvinylpyrrolidone film may be hard and brittle, a plasticizer may be added. As a plasticizer which may be added, ether ester derived plasticizers, glycerin or glycerin derived plasticizers, propylene glycol or glycol derived plasticizers, glycol ether derived plasticizers, polyhydroxycarboxylic acid derived plasticizers, phthalic acid derived plasticizers and the like can be mentioned as examples, but are is not limited to these.

In the method of manufacturing the microorganism culture sheet of the present invention, pattern-forming is done using the application liquid, but the culture layer can be particularly suitably formed by application with a dispenser or the like using the above mentioned application liquid.

As mentioned above, the culture layer may a a multilayer of two or more layers. For example, by laminating by pattern-forming an application liquid wherein gelling agent and nutrient component powders are dispersed in an alcohol solution of a polyvinylpyrrolidone on a base sheet, and next, pattern-forming an application liquid wherein a color indicator is dispersed or dissolved in an alcohol solution of a polyvinylpyrrolidone, it is possible to form a culture layer where the colony visibility is further improved. Further, in the present invention, in the case that the culture layer is two layers consisting of a first culture layer and a second culture layer, the pattern-forming may be carried out by different methods. For example, the first culture layer may be pattern-formed by application with a dispenser, and the pattern-forming of the second culture layer may be carried out using spraying or another method.

In the present invention, after pattern-forming the application liquid on the base sheet, the alcohol included in the application liquid is removed. It has been found that, by using a culture layer including a gelling agent or the like in polyvinylpyrrolidone, it is possible to observe and count microorganism colonies in the same way as for an agar medium, and further, the visibility is greatly improved. Further, the gelling agent is water-soluble, thus it has usually been coated onto a substrate after being prepared as an aqueous solution, but removal of the water requires a heating treatment at a high temperature and for a long time, and when preparing the aqueous solution, the viscosity is high, thus air bubbles or the like may be introduced. According to the present invention, a powder of the gelling agent or the like is dispersed in an alcohol solution of polyvinylpyrrolidone, thus the inclusion of bubbles can be avoided, and water is not used, thus the drying can be carried out at low temperature and for a short time. Further, the gelling agent or the like is only dispersed in the alcohol solution of the polyvinylpyrrolidone and is not dissolved, thus an increase in the viscosity of the application liquid can be prevented, and because of this it is possible to smoothly carry out pattern-forming. Moreover, in the obtained culture layer, the above mentioned components are coated in polyvinylpyrrolidone, thus when the test liquid is inoculated, the polyvinylpyrrolidone is immediately dissolved, and the above mentioned components are dissolved or absorb water. Therefore, after inoculating the test liquid, it is possible to immediately cover with the cover sheet. Further, in the case that the polyvinylpyrrolidone is dissolved, and the gelling agent is included, it thickens and adheres to the cover sheet, thus in addition to preventing drying, it is possible to ensure excellent visibility.

In the microorganism culture sheet of the present invention, if a specified component layer is formed at the cover sheet, a specified component solution comprising at least one selected from the group consisting of a gelling agent, nutrient component, color indicator, selective agent and substrate in a binder solution may be coated to form specified component layer. The coating method may be whole surface coating, or may be a pattern-forming. In the case of pattern-forming, it may be printing, application, coating, spraying or the like, in the same way as for the formation of the culture layer.

The drying of the culture layer may be drying based on a prior art method such as temperature, pressure or the like of provided that it can remove the alcohol included in the application liquid.

In the present invention, the thickness of the culture layer formed on top of the base sheet when dry is 50 to 1000 μm, preferably 200 to 600 μm. Further, the coated amount when dry is 5 to 400 $g/m^2$, preferably 100 to 300 $g/m^2$. Within the above range, it is possible for the culture layer to have the optimal viscosity for the growth of germs.

(ii) Formation of the Frame Layer

The microorganism culture sheet of the present invention may have a frame layer formed on the surface of the base sheet, at the outer boundary of the culture layer. The frame layer can be formed using a hydrophobic resin. Further, the method used to produce the frame layer is not relevant. It is also possible to use a base sheet having the frame layer formed in advance.

As the base sheet with a frame layer formed thereon, a base sheet having at least a hydrophobic resin on its surface, where the portion of the hydrophobic resin is embossed to form a convex portion in the form of the frame, may be mentioned. Moreover, by forming the culture layer inside of this convex portion, the microorganism culture sheet of the present invention can be manufactured. Further, it is also possible to emboss the location where the culture layer is formed with a recessed form, and to take the protruding portion formed at the outer boundary of the recessed portion as the frame layer.

As the method for forming the frame layer before forming the culture layer on the base sheet, for example, it is possible to cut out a predetermined shape of a hydrophobic resin plate and attach this to the base sheet as the frame layer. Furthermore, it is possible to use a method of using a thick hydrophobic resin plate as the base sheet, removing a portion in a recessed form which will form the culture layer, and taking the remaining portion as the frame layer; or to form a protruding portion as the shape of the frame and to form the culture layer inside of this protruding portion, and to take the protruding portion as the frame layer.

Further, as the hydrophobic resin, it is possible to use the above mentioned UV curable ink, hot melt, thermally foamed ink or UV foaming agent or the like, and form the frame layer by pattern-forming. This is a non-solvent system, and the pattern can be easily made by a dispenser applicator or the like, and is particularly preferable in that the curing is also easy.

In the case of forming the frame layer using the above mentioned UV curable ink or the like as the hydrophobic resin, it is also possible to dissolve the hydrophobic resin in an appropriate solvent, and pattern-form by printing, application, coating or the like. The printing method, in addition to screen printing, may also be gravure printing, relief printing, transfer printing, flexographic printing, and other printing methods. Further, it is also possible to use other methods such as bar coating by coating using a bar or the like, knife coating, coating such as die coating or the like, or application with a dispenser or the like, or other methods, in a predetermined shape.

If the hydrophobic resin is a UV curable ink or a UV foaming ink, after the pattern-forming, UV radiation is irradiated. As the UV irradiation conditions, the total intensity of 50 to 2000 $mJ/cm^2$, preferably 100 to 1000 $mJ/cm^2$, and it is possible to jointly use light and heating from a UV irradiation lamp. The width of the foamable irradiation conditions varies depending on the type of the foaming agent. In the case that it is not possible to ensure a predetermined height at once, it is possible to form the frame layer with a plurality of printings. As the UV irradiation lamp, it is possible to use a metal halide lamp, mercury lamp or the like.

In the case of forming the frame layer after forming the culture layer, it is possible to form the frame layer by pattern-forming using the above mentioned UV curable ink, hot melt, thermally foamed ink, UV foaming agent or the like. At this time, if the culture layer comprises a component which is degraded by the UV radiation, the culture layer is preferably covered with metal or the like at the time of UV irradiation.

Further, it is also possible to cut out a predetermined shape of a hydrophobic resin plate, and to form the frame layer by adhering this to the base sheet at the outer boundary of the culture layer on the base sheet where the culture layer is formed.

In the present invention, either the formation of the frame layer or the formation of the culture layer may be carried out first, but if the formation of the culture layer is carried out first, because the culture layer produced by pattern-forming is a thin layer, it is possible to easily form the frame layer after this. On the other hand, if the frame layer is formed first, it is possible to easily produce the culture layer by pattern-forming an application liquid inside the frame layer with a dispenser or the like.

In the case that the frame layer is formed on top of the base sheet, it is preferable that it be formed adhering to the culture layer at the outer boundary of the culture layer so that no gaps are formed between the frame layer and the culture layer. In the case of having gaps between the frame layer and the culture layer, when the test liquid is inoculated to the culture layer, the test liquid is retained in these gaps, and it may be difficult to uniformly spread the test liquid. In order to form the frame layer and the culture layer so that no gaps are formed, it is convenient to form the frame layer in advance, and to pattern-form the application liquid inside the frame layer. As the pattern-forming method, application with a dispenser is can be suitably carried out. In the prior art, it was difficult to form the frame layer and the culture layer without forming gaps, thus it is conjectured that, even when forming the frame layer, the frame layer was formed on the upper face of the culture layer. According to the present invention, it is made possible to pattern-form using an application liquid comprising at least one selected from the group consisting of a gelling agent, a nutrient component, a color indicator, a selective agent and a substrate in an alcohol solution of a polyvinylpyrrolidone, and because it is possible to pattern-form the culture layer at the inner portion of the frame layer without forming gaps, the test liquid can be uniformly spread, and it is possible to produce a high performance microorganism culture sheet.

(iii) Providing and Fixing the Cover Sheet

In the microorganism culture sheet of the present invention, cultivation is done with the culture layer covered with a cover sheet after inoculation of the test liquid onto the culture layer, thus it is operationally convenient for one part of the cover sheet to be provided fixed to the base sheet. However, in the case of a direct stamp or a wipe sample test or the like, the working efficiency may be increased if there is no cover sheet, thus may be used with the cover sheet removed.

In the case of constituting the cover sheet and the base sheet of the same member, a separately made cover sheet may be fixed and provided on the base sheet by heat sealing or laminate adhesion or the like, but as shown in the developed view of FIG. 9(a) and the cross sectional view of FIG. 9(b), the microorganism culture sheet may be formed by using the same material for the cover sheet and the base sheet, and forming the frame layer (20) and the culture layer (30) on a base sheet (10), with the cover sheet (40) and base sheet (10) being continuously provided, and folding the cover sheet (40). FIG. 9(c) shows a cross sectional view of this. According to this method, even if a specified component layer (30') or an adhesive layer (50) is formed on the cover sheet, because the base sheet (10) and the cover sheet (40) are continuously formed, it is possible to accurately and simply form the specified component layer (30') at a position facing the culture layer (30) on top of the base sheet (10).

Figure 10:
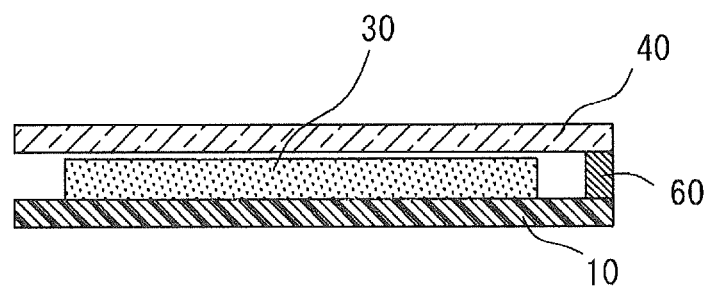
FIG. 10 is a drawing showing one example of the microorganism culture sheet according to the present invention and is cross sectional view showing a state where the cover sheet is provided fixed to the base sheet on which the culture layer is formed, by a double sided adhesive tape.
Figure 11:
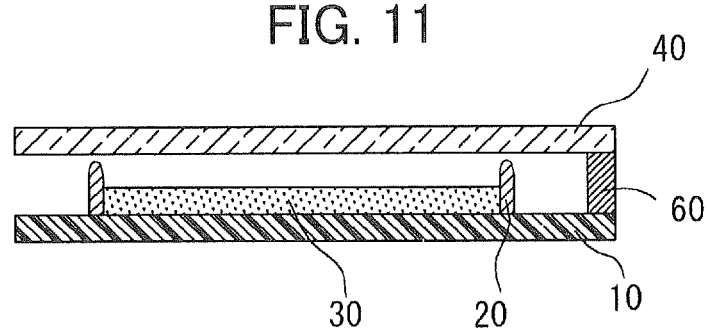
FIG. 11 is a drawing showing one example of the microorganism culture sheet according to the present invention and is cross sectional view showing a state where the cover sheet is provided fixed to the base sheet on which the culture layer and the frame layer are formed, by a double sided adhesive tape.

Further, as shown in the cross sectional views of FIG. 10 and FIG. 11, the cover sheet (40) and the base sheet (10) may be formed of different members, and the cover sheet (40) and the base sheet (10) on which the culture layer (30) is formed may be pasted with a double sided adhesive tape (60).

Figure 12:
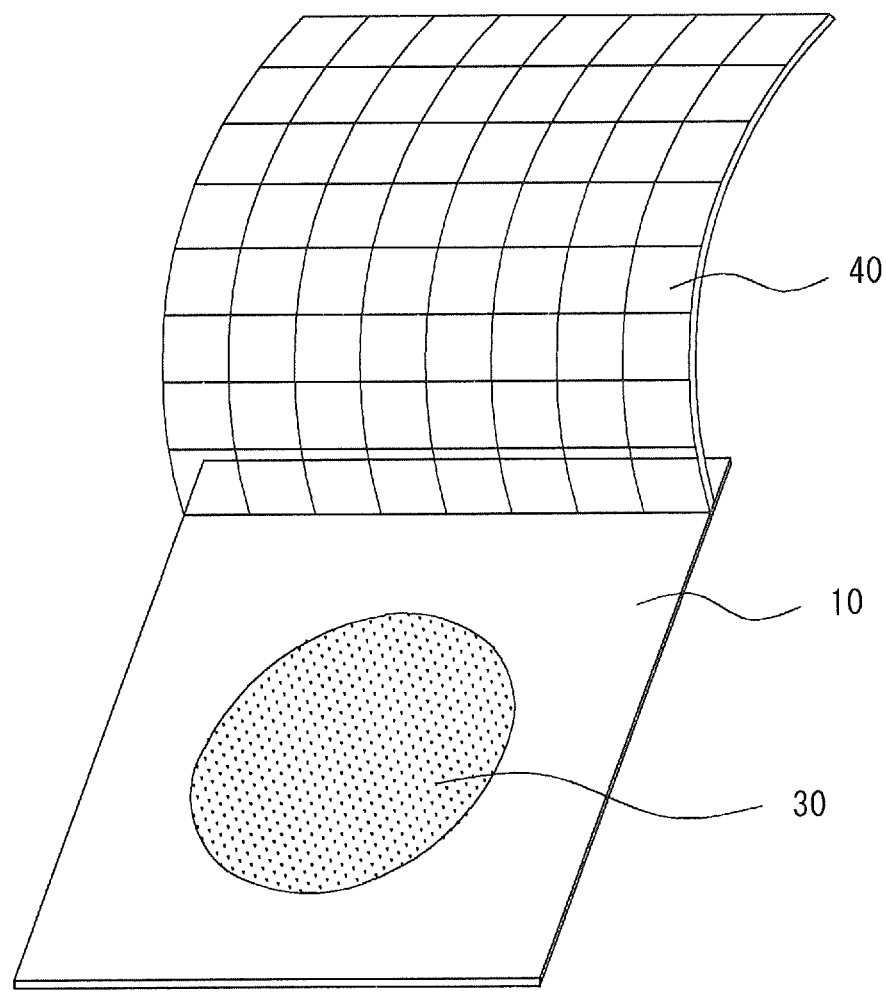
FIG. 12 is an exterior perspective view showing one example of the microorganism culture sheet according to the present invention.
Figure 13:
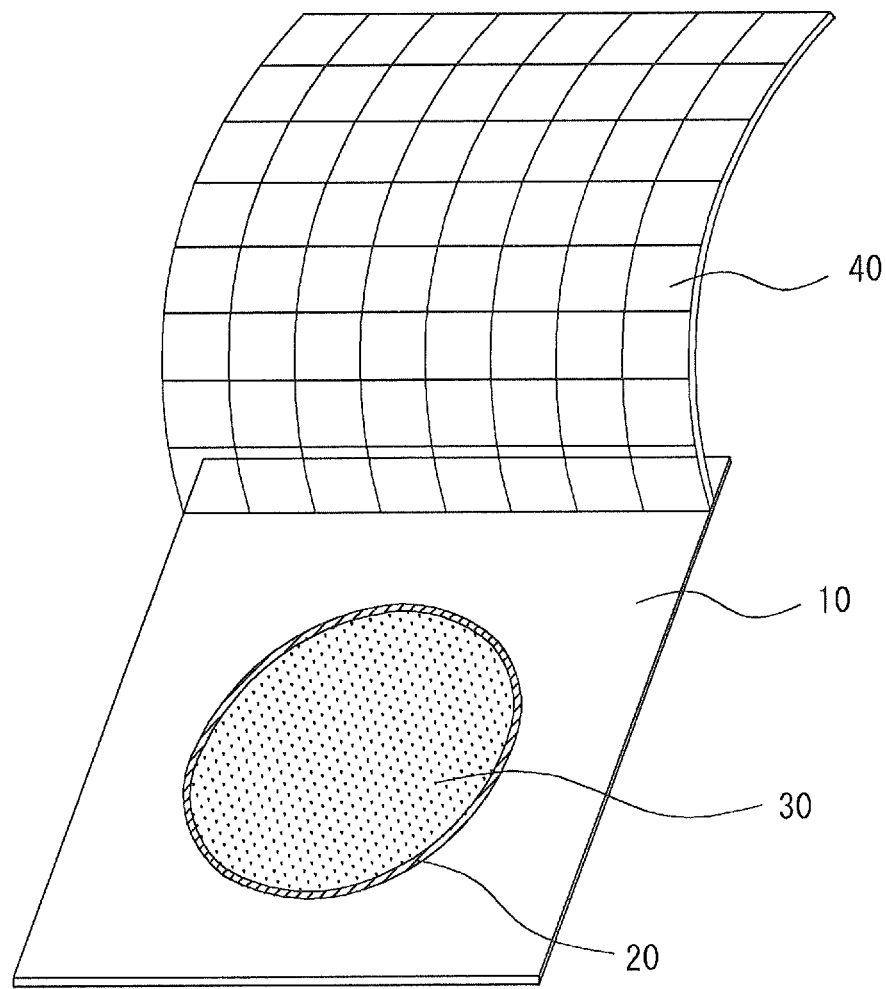
FIG. 13 is an exterior perspective view showing one example of the microorganism culture sheet according to the present invention where the frame layer is formed on top of the base sheet.

FIG. 12 and FIG. 13 show exterior perspective views of a microorganism culture sheet of the present invention where a grid pattern print is formed on the cover sheet (40), and the cover sheet (40) and the base sheet (10) on which the culture layer (30) is formed are adhered at the edge portions. In FIG. 13, a frame layer (20) is formed at the perimeter of the culture layer (30).

In the microorganism culture sheet of the present invention, sterilization such as gamma ray irradiation or ethylene oxide gas sterilization or the like is applied, to make the product of the microorganism culture sheet of the present invention. The microorganism culture sheet of the present invention makes it possible to carry out cultivation of various microorganisms depending on the type of included microorganism nutrient component, the air permeability of the used base sheet and cover sheet, etc.

EXAMPLES

The present invention is explained with reference to the following examples, but the present invention is not in any way limited to these examples.

Manufacturing Example 1

20 g of polyvinylpyrrolidone (manufactured by Nippon Shokubai, product name "Polyvinylpyrrolidone K-90") were dissolved in 130 g of methanol, and to this 60 g of guar gum powder (Sansho Co., Ltd., product name "Neovisco G", 200 mesh type) was dispersed, and furthermore, as a nutrient component, 20.16 g of tryptone (manufactured by Becton, Dickinson and Company, product name "BACT TRYPTONE"), 2.58 g of yeast extract (manufactured by Becton, Dickinson and Company, product name "YEAST EXTRACT"), 1.03 g of glucose (Wako Pure Chemical Industries, Ltd., product name "D-(+)-GLUCOSE") were mixed therewith to prepare an application liquid, and after pattern-forming with this application liquid the necessary portion on top of a polyethyleneterephthalate film (manufactured by Teijin Dupont Films, product name "Teijin Tetoron Film"), the culture layer was formed by drying for 15 min at 50° C. The thickness of the culture layer when dry was about 250 µm. Next, after applying a circular form with a width of 1.0 mm, a height of 750 µm, and a diameter of 52 mm of a UV curable ink (Jujo Chemical Co., Ltd., product name "Ray Cure GA 4100-2") using a dispenser, curing was performed by irradiating UV radiation with an integrated intensity of 250 mJ/cm$^2$ using a mercury lamp, to form a frame layer around the culture layer with a hydrophobic resin.

Then, a cover sheet (manufactured by Tohcello Inc., OPP film, product name "OP U-1 (single side corona discharge)", thickness 40 µm) was laminated on top of the above mentioned polyethyleneterephthalate film, and after adhering the edges, and disinfecting with γ rays, the microorganism culture sheet of the present invention was obtained.

Example 1

E. coli (ATCC 25922) were cultivated with shaking in a liquid culture medium (TRYPIC SOY BROTH) for 24 hours at 37° C. Then, the obtained test liquid was diluted with sterilized physiological saline solution such that the cell count was 10$^2$/ml, and TTC was added, to prepare the test liquid for cultivation tests. Then 1 ml of this test liquid for cultivation tests was inoculated with a sterilized pipet onto the culture layer of a microorganism culture sheet produced by the method of Manufacturing Example 1, the cover sheet was placed on top, and the test liquid spread to the entire culture layer. After this, gel formation was allowed with about one minute of still standing, and the cultivation test sample of Example 1 was obtained. Further, 5 cultivation test samples were made.

Example 2

The cultivation test sample of Example 2 was obtained by the same method as Example 1, except that the test liquid for cultivation tests was prepared by using K. pneumoniae (ATCC 13883) instead of E. coli as the strain.

Example 3

The cultivation test sample of Example 3 was obtained by the same method as Example 1, except that the test liquid for cultivation tests was prepared by using E. cloacae (ATCC 13536) instead of E. coli as the strain.

Example 4

The cultivation test sample of Example 4 was obtained by the same method as Example 1, except that the test liquid for cultivation tests was prepared by using *C. freundii* (JCM 1657) instead of *E. coli* as the strain.

Example 5

The cultivation test sample of Example 5 was obtained by the same method as Example 1, except that the test liquid for cultivation tests was prepared by using *S. aureus* (ATCC 25923) instead of *E. coli* as the strain.

Comparative Example 1

The cultivation test sample of Comparative Example 1 was obtained by adding 1 ml of the test liquid for cultivation tests of Example 1 to a petri dish, and pouring 20 ml of standard method agar prepared according to the pour plate method of the prior art.

Comparative Example 2

The cultivation test sample of Comparative Example 2 was obtained by the same method as Comparative Example 1, except that the test liquid for cultivation tests of Example 2 was used.

Comparative Example 3

The cultivation test sample of Comparative Example 3 was obtained by the same method as Comparative Example 1, except that the test liquid for cultivation tests of Example 3 was used.

Comparative Example 4

The cultivation test sample of Comparative Example 4 was obtained by the same method as Comparative Example 1, except that the test liquid for cultivation tests of Example 4 was used.

Comparative Example 5

The cultivation test sample of Comparative Example 5 was obtained by the same method as Comparative Example 1, except that the test liquid for cultivation tests of Example 5 was used.

[Cultivation Test]

Figure 14:
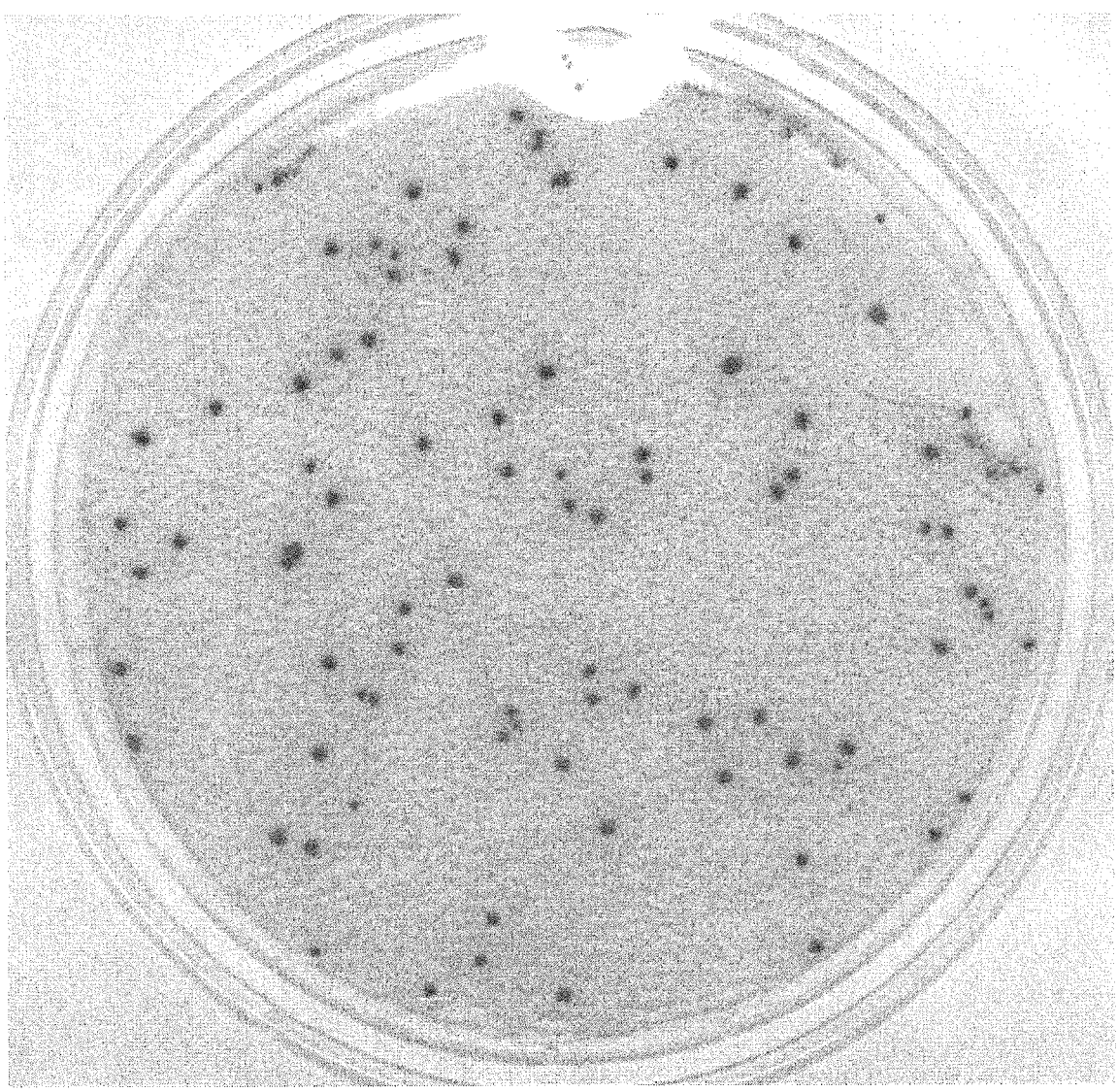
FIG. 14 is a drawing showing a state where colonies are generated on the microorganism culture sheet of Example 1.

The cultivation test samples of Examples 1 to 5 and of Comparative Examples 1 to 5 were put in an incubator, and cultivated for 48 hours at 37° C. Then, the number of colonies generated in each after cultivation was counted. Further, the colony generation state in the cultivation test sample of Example 1 using the microorganism culture sheet of the present invention is shown in FIG. 14.

When the number of colonies in the cultivation test samples of Examples 1 to 5 and the cultivation test samples of Comparative Examples 1 to 5 were compared, for all of the germs *E. coli, K. pneumoniae, E. cloacae, C. freundii,* and *S. aureus*, the correlation of the two was very good. Further, when observing the state of colony generation state of the cultivation test sample of Example 1 using the microorganism culture sheet of the present invention, the visibility was excellent (FIG. 14). It is considered that these results could be obtained according to the microorganism culture sheet of the present invention because the cover sheet and the culture layer are adhered by the thickened gelling agent and polyvinylpyrrolidone.

Manufacturing Example 2

On a polyethyleneterephthalate film (manufactured by Teijin Dupont, product name "Teijin Tetoron Film"), a thermoplastic resin (manufactured by Konishi Co., Ltd., product name "MP973") was applied using a dispenser in a circular form with a width of 1.0 mm, a height of 750 μm, and a diameter of 52 mm, to form the frame layer.

Next, 20 g of polyvinylpyrrolidone (manufactured by Nippon Shokubai, product name "Polyvinylpyrrolidone K-90") was dissolved in 210 ml methanol, 60 g of guar gum powder (Sansho Co., Ltd., product name "Neovisco G", 400 mesh type) was dispersed therein, and furthermore, as a nutrient component, 20.16 g of tryptone (manufactured by Becton, Dickinson and Company, product name "BACT TRYPTONE"), 2.58 g of yeast extract (manufactured by Becton, Dickinson and Company, product name "YEAST EXTRACT"), 1.03 g of glucose (Wako Pure Chemical Industries, Ltd., product name "D-(+)-GLUCOSE") were mixed therewith to prepare an application liquid.

After applying the application liquid containing this nutrient component and gelling agent inside the frame of the frame layer formed on the base material, using a dispenser, the culture layer was formed by drying for 15 min at 50° C. The thickness of the layer when dry was about 250 μm.

Then, a cover sheet (manufactured by Tohcello Inc., OPP film, product name "OP U-1 (single side corona discharge)", thickness 40 μm) printed with a grid pattern was laminated on top of the above mentioned polyethyleneterephthalate film, and after adhering the edges, and disinfecting with γ rays, the microorganism culture sheet of the present invention was obtained. Further, the height of the obtained frame layer was 750 μm (difference with the height of the culture layer: +500 μm), and its width was 1 mm.

Manufacturing Example 3

The microorganism culture sheet of the present invention was obtained by the same method as Manufacturing Example 2, except that a frame layer with a height of 600 μm was formed. Further, the height difference with the culture layer was +350 μm.

Manufacturing Example 4

The microorganism culture sheet of the present invention was obtained by the same method as Manufacturing Example 2, except that a frame layer with a height of 950 μm was formed. Further, the height difference with the culture layer was +700 μm.

Example 6

*E. coli* (ATCC 25922) were cultivated with shaking in a liquid culture medium (TRYPTIC SOY BROTH) for 24 hours at 37° C. Then, the obtained test liquid was diluted with sterilized physiological saline solution such that the cell count was $10^2$/ml, and TTC was added, to prepare the test liquid for cultivation tests. Then 1 ml of this test liquid for cultivation tests was inoculated with a sterilized pipet onto the culture layer of a microorganism culture sheet produced by the method of Manufacturing Example 2, the cover sheet was placed on top, and the test liquid spread to the entire culture layer inside the frame layer. After this, gel formation was allowed with about one minute of still standing, and the cultivation test sample of Example 6 was obtained. Further, 5 cultivation test samples were made.

Example 7

The cultivation test sample of Example 7 was obtained by the same method as Example 6, except that the test liquid for cultivation tests was prepared by using *K. pneumoniae* (ATCC 13883) instead of *E. coli* as the strain.

Example 8

The cultivation test sample of Example 8 was obtained by the same method as Example 6, except that the test liquid for cultivation tests was prepared by using *E. cloacae* (ATCC 13536) instead of *E. coli* as the strain.

Example 9

The cultivation test sample of Example 9 was obtained by the same method as Example 6, except that the test liquid for cultivation tests was prepared by using *C. freundii* (JCM 1657) instead of *E. coli* as the strain.

Example 10

The cultivation test sample of Example 10 was obtained by the same method as Example 6, except that the test liquid for cultivation tests was prepared by using *S. aureus* (ATCC 25923) instead of *E. coli* as the strain.

Comparative Example 6

The cultivation test sample of Comparative Example 6 was obtained by adding 1 ml of the test liquid for cultivation tests of Example 6 to a petri dish, and pouring 20 ml of standard method agar prepared according to the pour plate method of the prior art.

Comparative Example 7

The cultivation test sample of Comparative Example 7 was obtained by the same method as Comparative Example 6, except that the test liquid for cultivation tests of Example 7 was used.

Comparative Example 8

The cultivation test sample of Comparative Example 8 was obtained by the same method as Comparative Example 6, except that the test liquid for cultivation tests of Example 8 was used.

Comparative Example 9

The cultivation test sample of Comparative Example 9 was obtained by the same method as Comparative Example 6, except that the test liquid for cultivation tests of Example 9 was used.

Comparative Example 10

The cultivation test sample of Comparative Example 10 was obtained by the same method as Comparative Example 6, except that the test liquid for cultivation tests of Example 10 was used.

Example 11

The cultivation test sample of Example 11 was obtained by the same method as Example 6, except that the microorganism culture sheet produced by the method of Manufacturing Example 3 was used.

Example 12

The cultivation test sample of Example 12 was obtained by the same method as Example 6, except that the microorganism culture sheet produced by the method of Manufacturing Example 4 was used.

[Cultivation Test]

Figure 15:
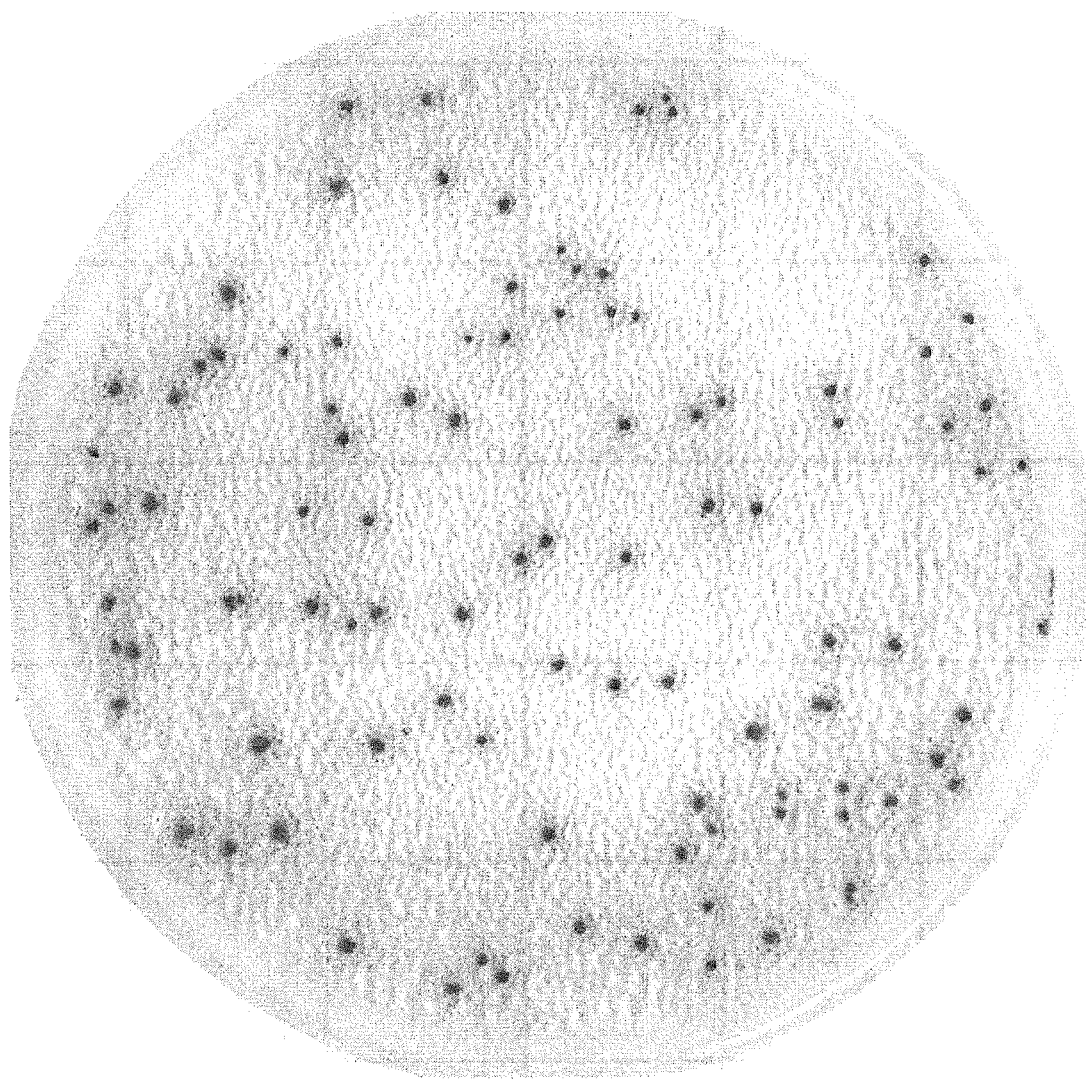
FIG. 15 is a drawing showing a state where colonies are generated on the microorganism culture sheet of Example 6.

The cultivation test samples of Examples 6 to 12 and of Comparative Examples 6 to 10 were put in an incubator, and cultivated for 48 hours at 37° C. Then, the number of colonies generated in each after cultivation was counted. The results of this are shown in Table 1. Further, the state of the colony generation in the cultivation test sample of Example 6 using the microorganism culture sheet of the present invention is shown in FIG. 15.

TABLE 1

| | Number of Colonies | | | | | |
|---|---|---|---|---|---|---|
| | 1 | 2 | 3 | 4 | 5 | Average |
| Example 6 | 87 | 92 | 82 | 90 | 95 | 89 |
| Comparative Example 6 | 87 | 97 | 95 | 89 | 89 | 91 |
| Example 7 | 116 | 121 | 115 | 135 | 120 | 121 |
| Comparative Example 7 | 98 | 109 | 114 | 120 | 115 | 111 |
| Example 8 | 106 | 90 | 90 | 106 | 93 | 97 |
| Comparative Example 8 | 94 | 103 | 95 | 110 | 98 | 100 |
| Example 9 | 83 | 73 | 85 | 76 | 93 | 82 |
| Comparative Example 9 | 64 | 57 | 68 | 62 | 68 | 64 |
| Example 10 | 92 | 112 | 95 | 120 | 103 | 104 |
| Comparative Example 10 | 53 | 41 | 61 | 58 | 66 | 56 |

When the number of colonies in the cultivation test samples of Examples 6 to 10 and the cultivation test samples of Comparative Examples 6 to 10 were compared, for all of the germs *E. coli, K. pneumoniae, E. cloacae, C. freundii,* and *S. aureus*, the correlation of the two was very good (Table 1). In Example 11 where the height of the frame layer is changed, the average colony number is 97, and further, in Example 12, the average colony number is 93, confirming that equivalent cultivation performance is exhibited within a stipulated range of frame layer height. Further, when observing the colony generation state of the cultivation test sample of Example 6 using the microorganism culture sheet of the present invention, the visibility was excellent (FIG. 15).

INDUSTRIAL APPLICABILITY

The microorganism culture sheet of the present invention can be used for cell count testing and the like, and is useful in having excellent operability and visibility.

The invention claimed is:
1. A microorganism culture sheet comprising:
a flat base sheet,
a culture layer of a predetermined shape formed on top of the base sheet, a thickness of the culture layer formed on top of the base sheet when dry is 50 to 1000 µm,
a frame layer that surrounds the culture layer, is formed directly on top of the flat base sheet, is formed at an outer boundary of the culture layer, the frame layer having a flat surface where the frame layer is formed directly on top of the flat base sheet and a rounded convex surface where the frame layer contacts a film cover sheet, and the film cover sheet contacts the rounded convex surface of the frame layer, covers the culture layer when closed, is adhered to a distal end of the base sheet, is made of plastic and has a thickness from 10 to 200 μm, wherein the height of the frame layer is higher than the height of the culture layer by 100 to 1200 μm, wherein the culture layer is formed by applying to the top of the base sheet, a liquid comprising a polyvinylpyrrolidone and at least one selected from the group consisting of a gelling agent, a nutrient component, a color indicator, a selective agent, and a substrate, and wherein the base sheet is larger in area than the frame layer in a top view of the microorganism culture sheet.

2. The microorganism culture sheet according to claim 1, wherein the application liquid comprises a polyvinylpyrrolidone and a gelling agent.

3. The microorganism culture sheet according to claim 1, wherein the frame layer consists of a hydrophobic resin.

4. The microorganism culture sheet according to claim 1 wherein the base sheet and/or the cover sheet consists of a transparent plastic sheet.

5. The microorganism culture sheet according to claim 1, wherein the base sheet is made of paper.

6. The microorganism culture sheet according to claim 1, wherein the base sheet is made of synthetic paper and the cover sheet is made of a member selected from the group consisting of polyolefin and polyester.

7. The microorganism culture sheet according to claim 1, wherein the cover sheet is waterproof and impermeable to water vapor.

8. The microorganism culture sheet according to claim 1, wherein the cover sheet is adhered to the base sheet by a double sided adhesive tape.

9. The microorganism culture sheet according to claim 1, wherein the cover sheet has two angled portions.

10. The microorganism culture sheet according to claim 1, wherein the cover sheet has a specified component layer formed thereon as to face a culture layer formed on the base sheet.

11. A microorganism culture sheet comprising:

a flat base sheet, a culture layer of a predetermined shape formed on top of the base sheet for culturing microorganisms, a thickness of the culture layer formed on top of the base sheet when dry is 50 to 1000 μm, a frame layer formed directly on top of the flat base sheet, formed before forming the culture layer on the flat base sheet formed at an outer boundary of the culture layer, the frame layer having a flat surface where the frame layer is formed directly on top of the flat base sheet and a rounded convex surface where the frame layer contacts a film cover sheet, and the film cover sheet, said film cover sheet contacts the rounded convex surface of the frame layer, is adhered at a distal edge portion of the base sheet for an operability of opening and closing of the cover sheet to cover the culture layer in a closed state and to lift off from the base sheet, except for the adhered edge portion, in an open state, and the film cover sheet is made of plastic and has a thickness from 10 to 200 μm, wherein the height of the frame layer is higher than the height of the culture layer by 100 to 1200 μm.

12. The microorganism culture sheet according to claim 11, wherein the cover sheet has a specified component layer formed thereon as to face a culture layer formed on the base sheet.

13. A microorganism culture sheet comprising:

a flat base sheet, a culture layer of a predetermined shape formed on top of the base sheet, a thickness of the culture layer formed on top of the base sheet when dry is 50 to 1000 μm, a frame layer that surrounds the culture layer, is adhered directly on top of the flat base sheet is formed at an outer boundary of the culture layer so that no gaps are formed between the frame layer and the culture layer, the frame layer having a flat surface where the frame layer is formed directly on top of the flat base sheet and a rounded convex surface where the frame layer contacts a film cover sheet, and the film cover sheet contacts the rounded convex surface of the frame layer, covers the culture layer when closed, is adhered to a distal end of the base sheet, is made of plastic and has a thickness from 10 to 200 μm, wherein the height of the frame layer is higher than the height of the culture layer by 100 to 1200 μm, wherein the culture layer is formed by applying to the top of the base sheet, a liquid comprising a polyvinylpyrrolidone and at least one selected from the group consisting of a gelling agent, a nutrient component, a color indicator, a selective agent, and a substrate, and wherein the base sheet is larger in area than the frame layer in a top view of the microorganism culture sheet.

14. The microorganism culture sheet according to claim 1, wherein the thickness of the cover sheet is from 20 to 70 μm.

15. The microorganism culture sheet according to claim 11, wherein the thickness of the cover sheet is from 20 to 70 μm.

16. The microorganism culture sheet according to claim 13, wherein the thickness of the cover sheet is from 20 to 70 μm.

17. The microorganism culture sheet according to claim 1, wherein the plastic of the cover sheet is made of polyolefins selected from the group consisting of polyethylene, polypropylene and the like, polyester, polyamide, polystyrene, polycarbonate, polyvinylchloride.

18. The microorganism culture sheet according to claim 11, wherein the plastic of the cover sheet is made of polyolefins selected from the group consisting of polyethylene, polypropylene and the like, polyester, polyamide, polystyrene, polycarbonate, polyvinylchloride.

19. The microorganism culture sheet according to claim 13, wherein the plastic of the cover sheet is made of polyolefins selected from the group consisting of polyethylene, polypropylene and the like, polyester, polyamide, polystyrene, polycarbonate, polyvinylchloride.

* * * * *